US009008851B2

(12) United States Patent   (10) Patent No.: US 9,008,851 B2
Hung et al.   (45) Date of Patent: Apr. 14, 2015

(54) CONTROL SYSTEM AND METHOD FOR INITIALIZING THE CONTROL SYSTEM

(75) Inventors: Yu-Wei Hung, Tainan (TW);
Yung-Ching Huang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 1058 days.

(21) Appl. No.: 13/046,702

(22) Filed: Mar. 12, 2011

(65) Prior Publication Data

US 2012/0166006 A1   Jun. 28, 2012

(30) Foreign Application Priority Data

Dec. 22, 2010   (TW) ................................ 99145272 A

(51) Int. Cl.
*A61B 5/00* (2006.01)
*A61B 5/11* (2006.01)
*A61G 7/057* (2006.01)

(52) U.S. Cl.
CPC ............. *A61B 5/1113* (2013.01); *A61B 5/6892* (2013.01); *A61G 7/057* (2013.01);
(Continued)

(58) Field of Classification Search
CPC ............... A61B 5/1113; A61B 5/6892; A61B 2562/046; A61B 2562/0247; A61B 5/1115; A61G 2203/32; A61G 7/057; A61G 2203/34
USPC .................................. 700/19, 22, 23, 24, 286
See application file for complete search history.

(56) References Cited

U.S. PATENT DOCUMENTS 5,010,772 A   4/1991   Bourland et al.
5,999,848 A *  12/1999   Gord et al. ......................... 607/2
(Continued)

FOREIGN PATENT DOCUMENTS

CN   2523166   11/2002
EP   1284556   2/2003
(Continued)

OTHER PUBLICATIONS

"Office Action of Taiwan Counterpart Application", issued on Oct. 25, 2013, p. 1-p. 5.
(Continued)

*Primary Examiner* — Mohammad Ali
*Assistant Examiner* — Nathan Laughlin
(74) *Attorney, Agent, or Firm* — Jianq Chyun IP Office

(57) ABSTRACT

A control system and a method for initializing the control system are provided. The control system includes a control platform and a plurality of target modules $SM_1 \sim SM_n$. Data transmission ends of the target modules are connected to the control platform. A power input end of the target module $SM_1$ receives an operation electrical energy. The target module $SM_1$ delays the operation electrical energy by a first period, and outputs the operation electrical energy via a power output end of the target modules $SM_1$. A power input end of the target module $SM_i$ receives the operation electrical energy from a power output end of the target module $SM_{(i-1)}$. The target module $SM_i$ delays the operation electrical energy by an $n^{th}$ period, and outputs the operation electrical energy via a power output end of the target modules $SM_i$, wherein $1 \le i \le n$.

27 Claims, 15 Drawing Sheets

(52) U.S. Cl.
CPC ...... *A61B 5/1115* (2013.01); *A61B 2562/0247* (2013.01); *A61B 2562/046* (2013.01); *A61G 2203/32* (2013.01); *A61G 2203/34* (2013.01)

(56) References Cited

U.S. PATENT DOCUMENTS

| | | | |
|---|---|---|---|
| 6,279,183 | B1 | 8/2001 | Kummer et al. |
| 6,764,446 | B2 | 7/2004 | Wolinsky et al. |
| 6,766,222 | B1 | 7/2004 | Duley |
| 7,010,473 | B1 | 3/2006 | Singh |
| 7,398,688 | B2 | 7/2008 | Zdeblick et al. |
| 7,726,209 | B2 | 6/2010 | Ruotoistenmaki |
| 2006/0009883 | A1* | 1/2006 | Takeichi et al. ............ 701/1 |
| 2008/0312846 | A1* | 12/2008 | Kessler et al. ............ 702/35 |
| 2009/0021955 | A1* | 1/2009 | Kuang et al. ............ 362/479 |
| 2009/0128061 | A1* | 5/2009 | Dilley et al. ............ 315/317 |
| 2014/0035481 | A1* | 2/2014 | Peting et al. ............ 315/291 |

FOREIGN PATENT DOCUMENTS

| | | |
|---|---|---|
| TW | 200409676 | 6/2004 |
| TW | I266046 | 11/2006 |
| TW | I306503 | 2/2009 |
| TW | 200935040 | 8/2009 |
| TW | 201007149 | 2/2010 |
| TW | I321402 | 3/2010 |

OTHER PUBLICATIONS

Townsend et al., "Measuring Chest Movement Using an Array of Unobstusive Pressure Sensors," 2010 IEEE Instrumentation and Measurement Technology Conference,p. 1053-1056, Sep. 6, 2010.

Klann et al., "Measurement of Spatial Cross Sections of Ultrasound Pressure Fields by Optical Scanning Means," 2005 IEEE Transactions on Ultrasonics, Ferroelectrics and Frequency Control, p. 1546-1554, Sep. 3, 2005.

Bock et al., "Coherence Multiplexing of Fiber-Optic Pressure and Temperature Sensors Based on Highly Birefringent Fibers," 1999 IEEE Transactions on Ultrasonics, Ferroelectrics and Frequency Control, p. 1541-1545.

* cited by examiner

CONTROL SYSTEM AND METHOD FOR INITIALIZING THE CONTROL SYSTEM

CROSS-REFERENCE TO RELATED APPLICATION

This application claims the priority benefit of Taiwan application serial no. 99145272, filed on Dec. 22, 2010. The entirety of the above-mentioned patent application is hereby incorporated by reference herein and made a part of this specification.

BACKGROUND

1. Field of the Disclosure

The disclosure relates to a control system. Particularly, the disclosure relates to a method for initializing a control system.

2. Description of Related Art

Along with tech-care application requirements, a control system is used to sense pressure information of a mat, a mattress or a cushion to detect specific activities of a user, for example, sleeping and leaving the bed, etc. In the conventional control system, a size of the mat, the mattress or the cushion, and a layout method of sensors and a number thereof in the mat, the mattress or the cushion are predetermined during a design stage thereof. When the conventional control system is applied in an actual product, since the product has a fixed size, it cannot be flexibly applied to the mattresses of the mats with different sizes.

SUMMARY OF THE DISCLOSURE

The disclosure is directed to a control system and a method for initializing the control system, the control system can be applied for a multipoint array sensing system (for example, a tech-care sensing system), a multipoint array control system (for example, a train car control system or a light emitting diode (LED) billboard, etc), or other control systems. Taking the tech-care sensing system as an example, the control system can be flexibly assembled as sensing areas (for example, a mattress or floor) of different sizes according to application and environment requirements. After the assembly, the control system can automatically detect patterns of a plurality of target modules, so that it can be applied for sensing mattresses and floor of different sizes.

An exemplary embodiment of the disclosure provides a control system including n target modules $SM_1$-$SM_n$. The target modules $SM_1$-$SM_n$ respectively have at least a data transmission end, at least a power input end and at least a power output end. The data transmission ends of the target modules $SM_1$-$SM_n$ are electrically connected to at least one control platform. The power input end of the target module $SM_1$ receives an operation electrical energy. The target module $SM_1$ delays the operation electrical energy by a first period, and outputs the operation electrical energy via the power output end of the target module $SM_1$. The power input end of the target module $SM_i$ receives the operation electrical energy from the power output end of the target module $SM_{(i-1)}$. The target module $SM_i$ delays the operation electrical energy by an $i^{th}$ period, and outputs the operation electrical energy via the power output end of the target module $SM_i$, wherein, n, i are integers, and $1 \le i \le n$.

An exemplary embodiment of the disclosure provides a method for initializing a control system. The control system includes n target modules $SM_1$-$SM_n$, and the target modules $SM_1$-$SM_n$ respectively have at least a data transmission end, at least a power input end and at least a power output end. The method for initializing the control system includes following steps. An operation electrical energy is supplied to the power input end of the target module $SM_1$. The operation electrical energy is delayed by a first period by the target module $SM_1$, and is output via the power output end of the target module $SM_1$. The operation electrical energy output from the power output end of the target module $SM_{(i-1)}$ is received by the power input end of the other target module $SM_i$. The operation electrical energy is delayed by an $i^{th}$ period by the target module $SM_i$, and is output via the power output end of the target module $SM_i$, wherein, n, i are integers, and $1 \le i \le n$.

An exemplary embodiment of the disclosure provides a control system including n target modules $SM_1$-$SM_n$. The target modules $SM_1$-$SM_n$ respectively have at least a data transmission end, at least a power input end, at least a power output end, at least a power enable end and at least a power control end. The data transmission ends of the target modules $SM_1$-$SM_n$ are electrically connected to at least one control platform. The power input end of the target module $SM_1$ receives an operation electrical energy, the power output end of the target module $SM_1$ outputs the operation electrical energy, and the power enable end of the target module $SM_1$ is electrically connected to the control platform. The power input end of the target module $SM_i$ receives the operation electrical energy from the power output end of the target module $SM_{(i-1)}$, the power output end of the target module $SM_i$ outputs the operation electrical energy, and the power enable end of the target module $SM_i$ is electrically connected to the power control end of the target module $SM_{(i-1)}$, wherein n, i are integers, and $1 \le i \le n$. It is determined whether or not to activate each of the target modules $SM_i$ according to control of the power enable end, and the power control end outputs a power enable signal after the target module $SM_i$ is activated for an $i^{th}$ period.

According to the above descriptions, the exemplary embodiment of the disclosure provides a detachable control system. The control system includes n target modules. By supplying the operation electrical energy in timing, the target modules respectively transmit an initialization packet to a control platform in tandem at different time. According to a time sequence of the initialization packets and determination of a message waiting time, the control platform can automatically detect geometric patterns of the target modules. Taking a sensing system as an example, based on the control system and the method of initilizing the control system of the disclosure, a user can flexibly assemble a plurality of target modules into sensing areas of different sizes according to application and environment requirements.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1A:
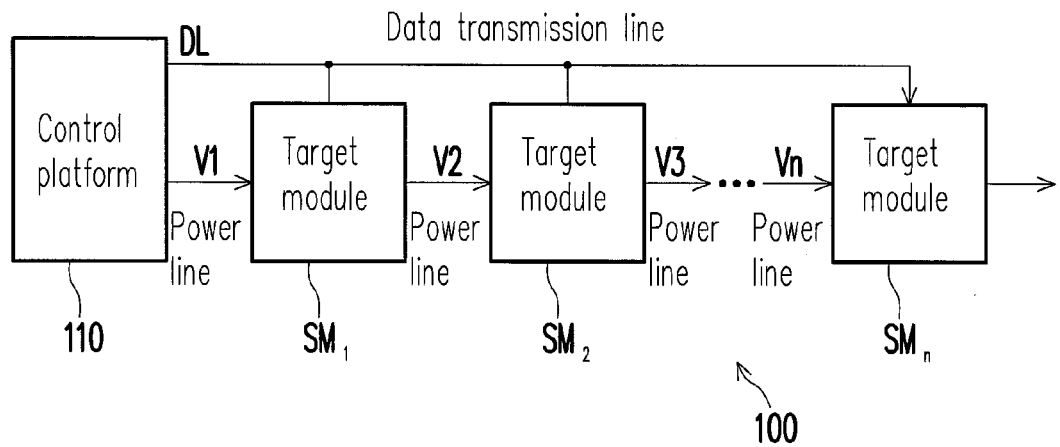
FIG. 1A is a functional block schematic diagram of a control system according to an exemplary embodiment of the disclosure.

FIG. 1A is a functional block schematic diagram of a control system 100 according to an exemplary embodiment of the disclosure. The control system 100 includes a control platform 110 and target modules $SM_1$-$SM_n$, where n is an integer. The target modules $SM_1$-$SM_n$ respectively have at least a data transmission end, at least a power input end and at least a power output end. The data transmission ends of the target modules $SM_1$-$SM_n$ are electrically connected to the control platform 110 through a data transmission line DL.

Figure 1B:
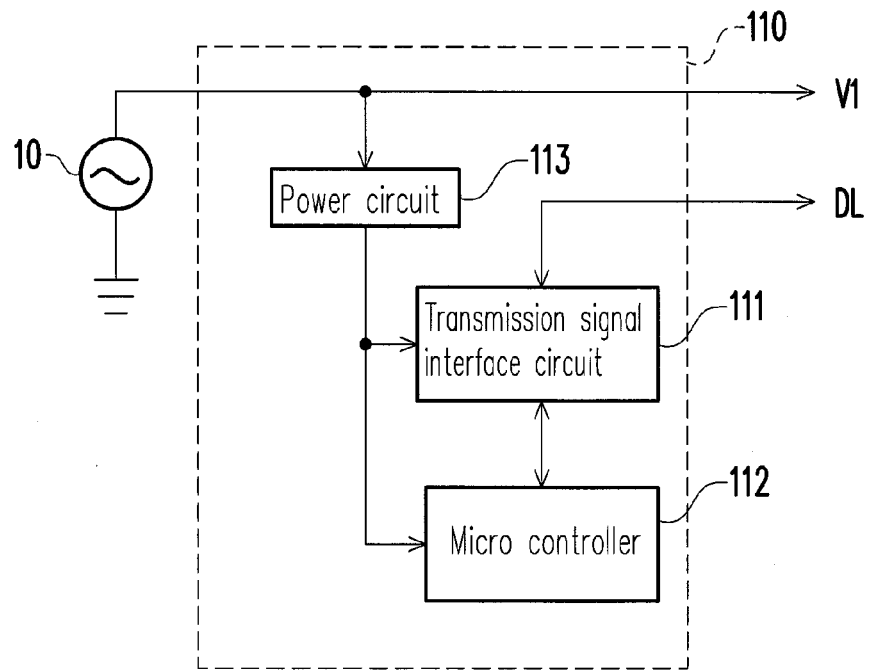
FIG. 1B is a functional block schematic diagram of a control platform of FIG. 1A according to an exemplary embodiment of the disclosure.

FIG. 1B is a functional block schematic diagram of the control platform 110 of FIG. 1A according to an exemplary embodiment of the disclosure. The control platform 110 includes a signal transmission interface circuit 111, a micro controller 112 and a power circuit 113. A power supply 10 shown in FIG. 1B can be a commercial power or an adapter, and the power circuit 113 can be a voltage regulator. The power supply 10 provides an operation electrical energy to a power line V1 and the power circuit 113. The power circuit 113 receives the operation electrical energy provided by the power supply 10, and provides the operation electrical energy to the signal transmission interface circuit 111 and the micro controller 112. The micro controller 112 transmits a communication packet to the data transmission line DL through the signal transmission interface circuit 111, and receives initialization packets and data packets transmitted by the target modules $SM_1$-$SM_n$ from the data transmission line DL through the signal transmission interface circuit 111.

Figure 2:
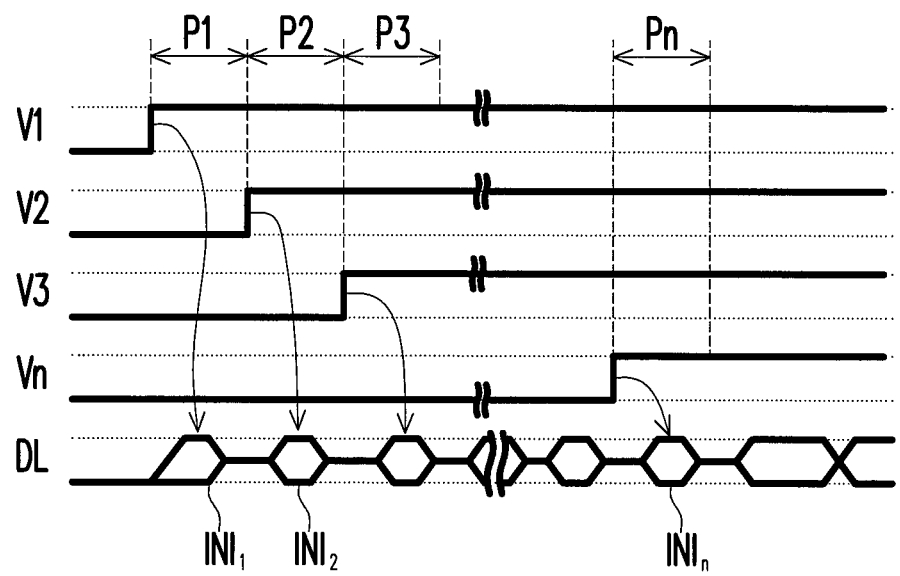
FIG. 2 is a signal timing diagram of the control system 100 of FIG. 1A according to an exemplary embodiment of the disclosure.

FIG. 2 is a signal timing diagram of the control system 100 of FIG. 1A according to an exemplary embodiment of the disclosure. Referring to FIG. 1A and FIG. 2, the power input end of the target module $SM_1$ receives the operation electrical energy through the power line V1, and the target module $SM_1$ delays the operation electrical energy by a first period P1, and outputs the operation electrical energy to a power line V2 via the power output end of the target module $SM_1$, where the operation electrical energy is the electrical energy required for operating the target module $SM_1$. In the embodiment of FIG. 1A, the control platform 110 supplies the operation electrical energy to the power input end of the target module $SM_1$ through the power line V1. In other embodiments, the operation electrical energy supplied to the power input end of the target module $SM_1$ can be provided by other devices, for example, a power supplier, etc.

The power input end of the target module $SM_i$ receives the operation electrical energy from the power output end of the target module $SM_{(i-1)}$ of the previous stage. The target module $SM_i$ delays the operation electrical energy by an $i^{th}$ period Pi, and outputs the operation electrical energy via the power output end of the target module $SM_i$, wherein i is an integer, and $1 \le i \le n$. The operation electrical energy is the electrical energy required for operating the target module $SM_i$. For example, the power input end of the target module $SM_2$ receives the operation electrical energy from the power output end of the target module $SM_1$ of the previous stage through the power line V2, and the target module $SM_2$ delays the operation electrical energy by a second period P2, and outputs the operation electrical energy to a power line V3 via the power output end of the target module $SM_2$. Deduced by analogy, the power input end of the target module $SM_n$ receives the operation electrical energy from the power output end of the target module $SM_{(n-1)}$ of the previous stage through a power line Vn, and the target module $SM_n$ delays the operation electrical energy by an $n^{th}$ period, and outputs the operation electrical energy via the power output end of the target module $SM_n$.

During an initial stage of a powered period that the power input end of the target module $SM_i$ receives the operation electrical energy, the target module $SM_i$ transmits an initialization packet $INI_i$ to the control platform 110 through the data transmission end of the target module $SM_i$. The $i^{th}$ period Pi includes a time period required for preparing the initialization packet $INI_i$ by the target module $SM_i$. For example, after the target module $SM_1$ is powered, it prepares the initialization packet $INI_1$ during the first period P1, and transmits the initialization packet $INI_1$ to the control platform 110 through the data transmission end and the data transmission line DL. After the initialization packet $INI_1$ is prepared, the target module $SM_1$ outputs the operation electrical energy to the target module $SM_2$ through the power output end and the power line V2. After the target module $SM_2$ is powered, it prepares an initialization packet $INI_2$ during the second period P2, and transmits the initialization packet $INI_2$ to the control platform 110 through the data transmission end and the data transmission line DL. After the initialization packet $INI_2$ is prepared, the target module $SM_2$ outputs the operation electrical energy to the next target module through the power output end and the power line V3. Deduced by analogy, after the target module $SM_n$ is powered, it prepares an initialization packet $INI_n$ during the $n^{th}$ period Pn, and transmits the initialization packet $INI_n$ to the control platform 110 through the data transmission end and the data transmission line DL.

The initialization packets $INI_1$-$INI_n$ respectively have a unique identification code (or other identification information) of the corresponding target module. Due to differences of power supplying time, the target modules $SM_1$-$SM_n$ sequentially transmit the initialization packets $INI_1$-$INI_n$ having the identification codes to the control platform 110 at different time according to layout positions thereof. The control platform 110 can obtain and record the layout positions of the target modules $SM_1$-$SM_n$ according to a time sequence that the target modules $SM_1$-$SM_n$ output the initialization packets $INI_1$-$INI_n$. For example, the control platform 110 can record the corresponding identification codes into a mapping table according to a time sequence for receiving the initialization packets $INI_1$-$INI_n$. After all of the target modules $SM_1$-$SM_n$ are initialized, the control platform 110 can analyse the layout position of the post-received data packets of the target modules according to the mapping table. Namely, the control platform 110 can automatically detect geometric patterns of the target modules $SM_1$-$SM_n$.

The control system 100 can be a multipoint array sensing system (for example, a tech-care sensing system or a security line sensing system, etc.), a multipoint array control system (for example, a train car control system or a light emitting diode (LED) lightbox control system, etc.) or other control systems. Taking an application of the train car control as an example, the control system 100 can be a car control system of multiple cars, and the target modules $SM_1$-$SM_n$ can be the cars. As described above, when the power is turned on, the cars (the target modules) send the initialization packets $INI_1$-$INI_n$ to the control platform 110 in tandem due to differences of power supplying time. The control platform 110 can record a connection sequence of the cars in the mapping table according to a time sequence that the cars send the initialization packets $INI_1$-$INI_n$. Therefore, when any of the cars sends a data packet to the control platform 110, the control platform 110 can obtain a layout position of the car according to the mapping table. Alternatively, the control platform 110 can obtain an identification code of a car of a certain position from the mapping table, and sends a control command packet having the identification code to the designated car.

Taking an application of the LED lightbox control as an example, the control system 100 can be a lightbox control system having a plurality of LED modules, and the target modules $SM_1$-$SM_n$ can be the LED modules. After the power is turned on, the LED modules (the target modules) send the initialization packets $INI_1$-$INI_n$ to the control platform 110 in tandem due to differences of power supplying time. The control platform 110 can record a connection sequence of the LED modules in the mapping table according to a time sequence that the LED modules send the initialization packets $INI_1$-$INI_n$. Therefore, the control platform 110 can obtain an identification code of a LED module of a certain position from the mapping table, and sends a control command packet having the identification code to the designated LED module.

Figure 3:
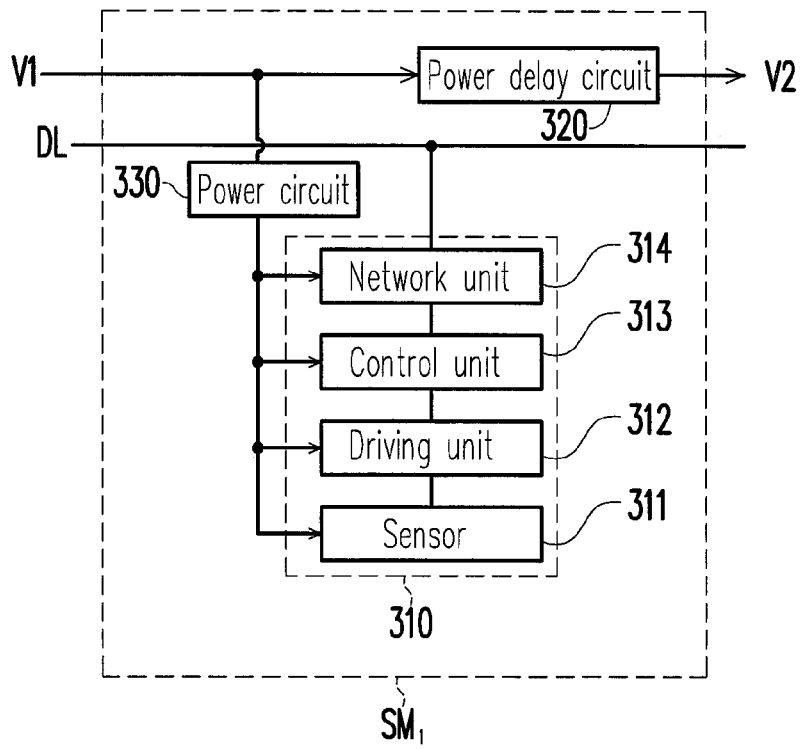
FIG. 3 is an internal functional block schematic diagram of a target module $SM_1$ of FIG. 1A according to an exemplary embodiment of the disclosure.

Taking an application of the tech-care as an example, the control system 100 can be a health care sensing system having a plurality of sensing modules, and the target modules $SM_1$-$SM_n$ can be pressure sensing modules. Therefore, the user can flexibly assemble an arbitrary number of the target modules $SM_1$-$SM_n$ into sensing areas of different sizes according to application and environment requirements. Implementations of the target modules $SM_1$-$SM_n$ are determined according to an actual design requirement. For example, FIG. 3 is an internal functional block schematic diagram of the target module $SM_1$ of FIG. 1A according to an exemplary embodiment of the disclosure. Implementations of the other target modules $SM_2$-$SM_n$ can be deduced according to related descriptions of the target module $SM_1$ of FIG. 3. The target module $SM_1$ includes a sensing unit 310, a power delay circuit 320 and a power circuit 330. The power circuit 330 can be a voltage regulator. The sensing unit 310 is connected to the data transmission end of the target module $SM_1$.

The power input end of the target module $SM_1$ receives the operation electrical energy provided by the power line V1, and supplies the operation electrical energy to the power circuit 330 and an input end of the power delay circuit 320. The power circuit 330 receives the operation electrical energy provided by the power line V1, and supplies the operation electrical energy to the sensing unit 310. In other embodiments, the power circuit 330 can be omitted to reduce cost, and the power line V1 is used to directly provide the operation electrical energy to the sensing unit 310. After delaying by the first period P1, the power delay circuit 320 supplies the operation electrical energy to the power output end of the target module $SM_1$ through an output end of the power delay circuit 320, and supplies the operation electrical energy to the target module $SM_2$ of the next stage through the power line V2. In the present embodiment, a delay-on relay or other techniques can be used to implement the power delay circuit 320. The relay well known by those skilled in the art can be one of the implementations of the power delay circuit 320 of the present exemplary embodiment.

Figure 4:
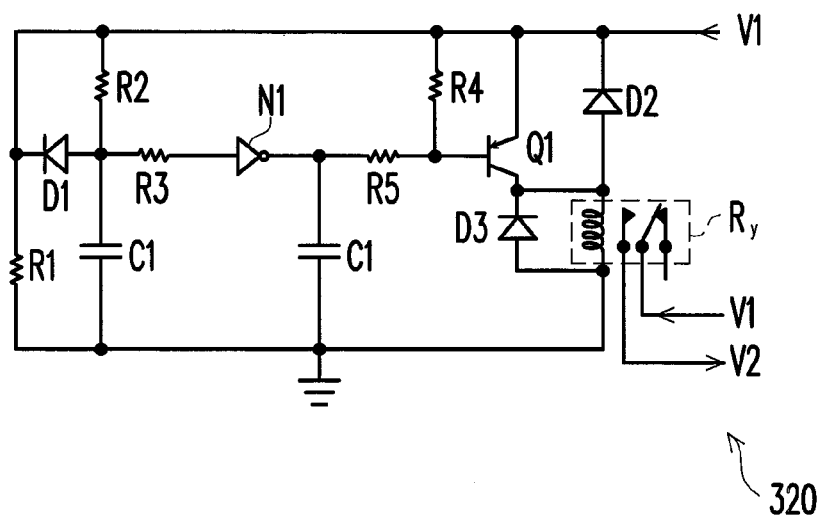
FIG. 4 is a circuit schematic diagram of a power delay circuit of FIG. 3 implemented by a delay-on relay.

The aforementioned delay-on relay can be any relay having a delay conducting function. For example, FIG. 4 is a circuit schematic diagram of a power delay circuit 320 of FIG. 3 implemented by a delay-on relay. The delay-on relay includes diodes D1-D3, resistors R1-R5, capacitors C1-C2, a NOT gate N1, a PNP transistor Q1 and a relay Ry, as that shown in FIG. 4. By adjusting resistances of the resistors R1-R5 and capacitances of the capacitors C1-C2, a delay time (i.e. a time length of the first period P1) of the power delay circuit 320 is adjusted. A moving contact (a movable armature) of the relay Ry is connected to the power line V1, and a normally opened contact of the relay Ry is connected to the power line V2. When the power line V1 is not supplied with the operation electrical energy, the moving contact and the normally opened contact of the relay Ry are not conducted. After the power line V1 is supplied with the operation electrical energy, during the first period P1, the moving contact and the normally opened contact of the relay Ry are still not conducted. After the first period P1 is ended, the moving contact and the normally opened contact of the relay Ry are conducted, and the operation electrical energy of the power line V1 can be transmitted to the power line V2 through the power delay circuit 320.

Referring to FIG. 3, the sensing unit 310 includes at least a sensor 311, a driving unit 312, a control unit 313 and a network unit 314. The power input end of the target module $SM_1$ receives the operation electrical energy provided by the power line V1, and supplies the operation electrical energy to the sensor 311, the driving unit 312, the control unit 313 and the network unit 314.

In other embodiments, if the control system 100 is applied to the LED lightbox control, a LED array can be used to replace the sensor 311, and a corresponding LED driving circuit is used to implement the driving unit 312. The control platform 110 can obtain an identification code of a LED module (the target module) of a certain position from the mapping table, and sends a control command packet having the identification code to the designated LED module (for example, the target module $SM_1$). The control unit 313 receives the control command packet from the control platform 110 through the network unit 314, and drives the LED array through the driving unit 312 according to the control command.

In the present embodiment, those skilled in the art can use any type of sensor to implement the sensor 311 according to application and design requirements. For example, if the control system 100 is applied to assembly-type floor mats capable of being assembled and disassembled, one or a plurality of pressure sensors can be equally disposed in each of the floor mats (i.e. the target module $SM_j$) to serve as the sensor 311. In other embodiments, the sensor 311 can be a light sensor, a temperature sensor, an electric/magnetic sensor, or other types of sensor. Based on the type of the sensor 311, the driving unit 312 may have a corresponding circuit design. The sensor 311 and the driving unit 312 are well known techniques of the art, which are not repeated herein. Moreover, a layout of the sensors 311 in the target module $SM_1$ and a number thereof can be determined according to an actual product design requirement.

The driving unit 312 drives/detects the sensor 311 to obtain a sensing result. The control unit 313 (for example, a micro controller) is connected to the driving unit 312, and receives the sensing result from the driving unit 312 for calculation/processing, and sends the processed sensing result and the identification code of the target module $SM_1$ to the network unit 314. The network unit 314 is connected to the control unit 313 and the data transmission end of the target module $SM_1$. The network unit 314 transmits the sensing result provided by the control unit 313 to the control platform 110 through the data transmission end and the data transmission line DL. A communication protocol between the network unit 314 and the control platform 110 can be determined according to an actual product design requirement.

During an initial stage that the power line V1 supplies the operation electrical energy to the sensor 311, the driving unit 312, the control unit 313 and the network unit 314, the control unit 313 establishes the initialization packet $INI_1$, and transmits the initialization packet $INI_1$ to the control platform 110 through the network unit 314 and the data transmission line DL. The initialization packet $INI_1$ has the identification code of the target module $SM_1$. After the initialization is completed, the control unit 313 obtains the sensing result of the sensor 311 through the driving unit 312, and transmits the sensing result to the control platform 110 through the network unit 314 and the data transmission line DL.

Figure 5:
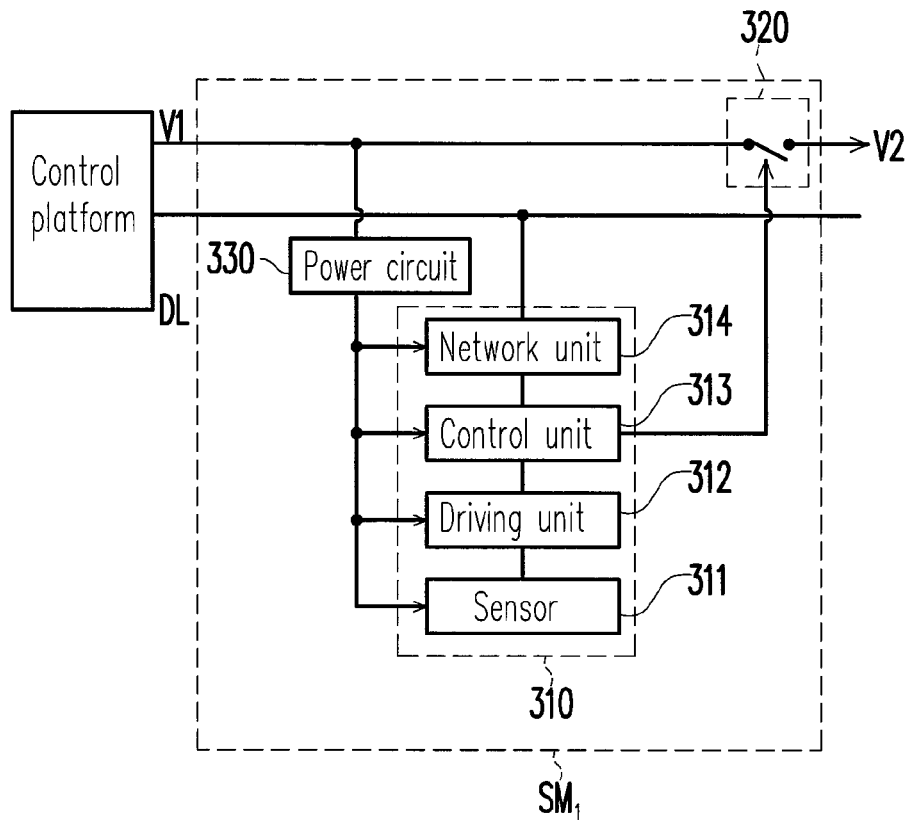
FIG. 5 is an internal functional block schematic diagram of the target module $SM_1$ of FIG. 1A according to another exemplary embodiment of the disclosure.

FIG. 5 is an internal functional block schematic diagram of the target module $SM_1$ of FIG. 1A according to another exemplary embodiment of the disclosure. Implementations of the other target modules $SM_2$-$SM_n$ can be deduced according to related descriptions of the target module $SM_1$ of FIG. 5. The embodiment FIG. 5 is similar to that of FIG. 3, and a difference there between lies in implementation of the power delay circuit 320. Here, the power delay circuit 320 is implemented by a controlled switch, and the controlled switch is controlled by the control unit 313, as that shown in FIG. 5. Two ends of the controlled switch are respectively connected to the power input end and the power output end of the target module $SM_1$, and a control end of the controlled switch is connected to the control unit 313. During the initial stage (i.e. the first period P1) that the power line V1 supplies the operation electrical energy to the control unit 313, the control unit 313 turns off the controlled switch and establishes the initialization packet $INI_1$. After the first period is ended, the control unit 313 has completed transmitting the initialization packet $INI_1$, and the control unit 313 turns on the controlled switch.

Figure 6:
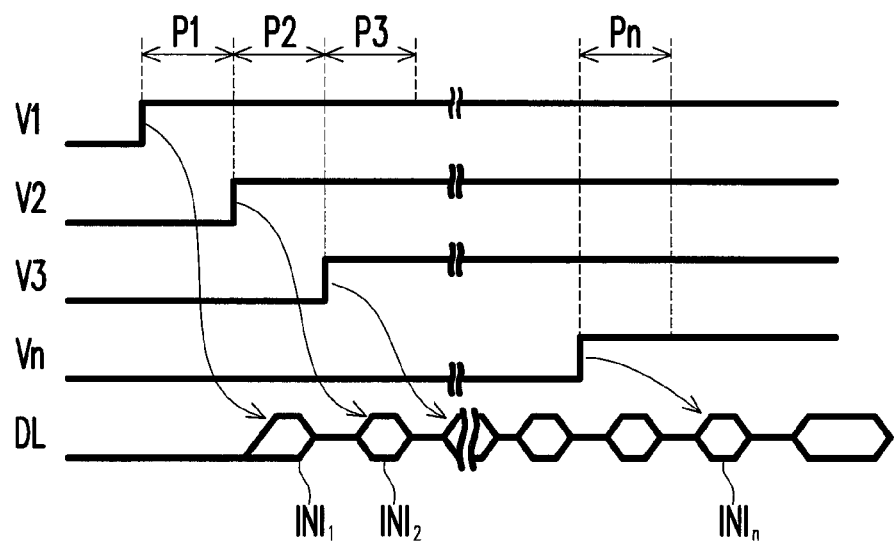
FIG. 6 is a signal timing diagram of the control system 100 of FIG. 1A according to another exemplary embodiment of the disclosure.

FIG. 6 is a signal timing diagram of the control system 100 of FIG. 1A according to another exemplary embodiment of the disclosure. The embodiment of FIG. 6 is similar to that of FIG. 2, and a difference there between lies in timings that the internal circuits of the target modules $SM_1$-$SM_n$ of the embodiment of FIG. 6 are powered and timings for preparing the initialization packets Referring to FIG. 1A and FIG. 6, during an initial stage of a powering period that the power output end of the target module $SM_i$ outputs the operation electrical energy, the target module $SM_i$ transmits the initialization packet $INT_i$ to control platform 110 through the data transmission end of the target module $SM_i$, where the $i^{th}$ period Pi includes a time required for preparing the initialization packet $INI_{(i-1)}$ by the previous target module $SM_{(i-1)}$.

For example, during an initial stage of a period that the power input end of the target module $SM_1$ is powered, the internal circuit of the target module $SM_1$ is still not powered. When the first period P1 is ended, the power output end of the target module $SM_1$ and the internal circuit thereof are supplied with the operation electrical energy, and now the internal circuit of the target module $SM_1$ starts to prepare the initialization packet $INI_1$, and the power output end of the target module $SM_1$ transmits the operation electrical energy to the target module $SM_2$ of the next stage through the power line V2. Therefore, the target module $SM_1$ completes preparing the initialization packet $INI_1$ during the second period P2 after the first period P1 is ended, and transmits the initialization packet $INI_1$ to the control platform 110 through the data transmission end and the data transmission line DL. Deduced by analogy, the target module $SM_2$ completes preparing the initialization packet $INI_2$ during the initial stage of the third period P3, and transmits the initialization packet $INI_2$ to the control platform 110 through the data transmission end and the data transmission line DL. The target module $SM_n$ completes preparing the initialization packet $INI_n$ after the $n^{th}$ period Pn is ended, and transmits the initialization packet $INI_n$ to the control platform 110 through the data transmission end and the data transmission line DL. Therefore, the control platform 110 can obtain and record the layout position of the target modules $SM_1$-$SM_n$ according to a time sequence that the target modules $SM_1$-$SM_n$ output the initialization packets $INI_1$-$INI_n$.

Figure 7:
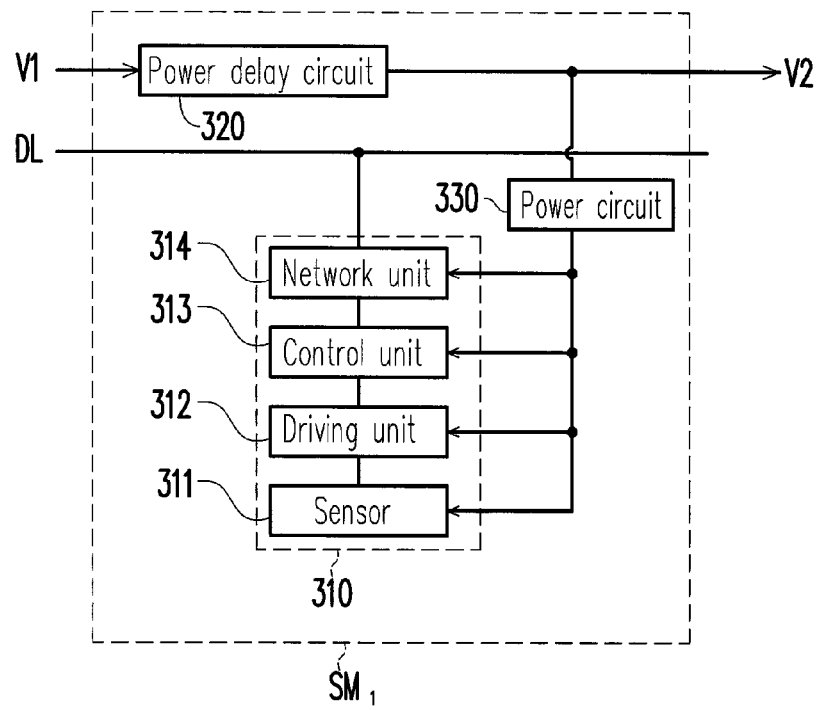
FIG. 7 is an internal functional block schematic diagram of the target module $SM_1$ of FIG. 1A according to still another exemplary embodiment of the disclosure.

In the embodiment of FIG. 6, implementations of the target modules $SM_1$-$SM_n$ are determined according to an actual design requirement. For example, FIG. 7 is an internal functional block schematic diagram of the target module $SM_1$ of FIG. 1A according to still another exemplary embodiment of the disclosure. Implementations of the other target modules $SM_2$-$SM_n$ can be deduced according to related descriptions of the target module $SM_1$ of FIG. 7. The target module $SM_1$ includes the sensing unit 310, the power delay circuit 320 and the power circuit 330. The embodiment of FIG. 7 is similar to that of FIG. 3, and a difference there between lies in a connection method of the power delay circuit 320.

Referring to FIG. 7, the sensing unit 310 is connected to the data transmission end of the target module $SM_1$. The input end of the power delay circuit 320 is connected to the power input end of the target module $SM_1$ for receiving the operation electrical energy transmitted by the power line V1. After delaying the operation electrical energy by the first period P1, the power delay circuit 320 supplies the delayed operation electrical energy to the power circuit 330 and the power output end of the target module $SM_1$ through the output end thereof. The power circuit 330 receives the operation electrical energy provided by the power delay circuit 320, and supplies the operation electrical energy to the sensing unit 310. Therefore, the target module $SM_2$ receives the operation electrical energy through the power line V2 after the first period P1 is ended, as that shown in FIG. 6. In the present exemplary embodiment, the output end of the power delay circuit 320 supplies the delayed operation electrical energy to the sensor 311, the driving unit 312, the control unit 313 and the network unit 314 through the power circuit 330. Therefore, the control unit 313 of the target module $SM_1$ is powered to function after the first period P1 is ended, and completes preparing the initialization packet $INI_1$ during the second period P2 after the first period P1 is ended, as that shown in FIG. 6.

Figure 8:
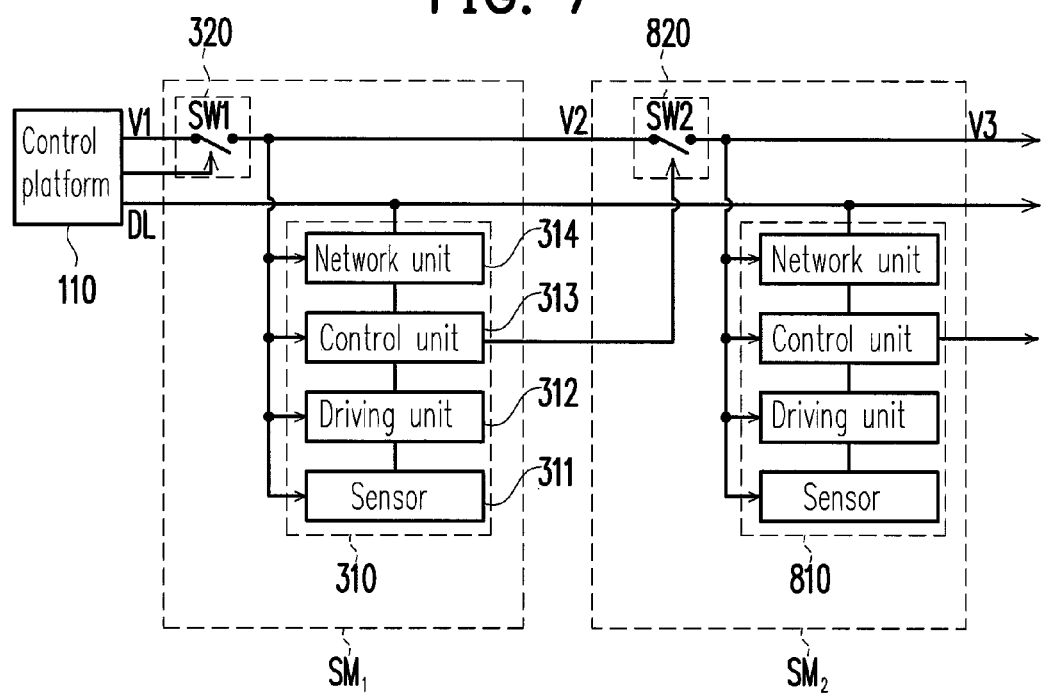
FIG. 8 is an internal functional block schematic diagram of the target module $SM_1$ of FIG. 1A according to yet another exemplary embodiment of the disclosure.

FIG. 8 is an internal functional block schematic diagram of the target module $SM_1$ of FIG. 1A according to yet another exemplary embodiment of the disclosure. Implementations of the other target modules $SM_2$-$SM_n$ can be deduced according to related descriptions of the target module $SM_1$ of FIG. 8. The embodiment of FIG. 8 is similar to that of FIG. 7, and a difference there between lies in implementation of the power delay circuit 320. Related descriptions of FIG. 5 can be referred for the power delay circuit 320 of FIG. 8. Here, the power delay circuit 320 of the target module $SM_1$ is implemented by a controlled switch SW1. Besides the controlled switch SW1 of the first target module $SM_1$, the controlled switch of the other target module $SM_i$ is controlled by the control unit of the target module $SM_{(i-1)}$ of the previous stage. For example, a controlled switch SW2 in a power delay circuit 820 of the target module $SM_2$ is controlled by the control unit 313 of the target module $SM_1$ of the previous stage, as that shown in FIG. 8.

In the present exemplary embodiment, the controlled switch SW1 of the target module $SM_1$ is controlled by the control platform 110. After the controlled switch SW1 is turned on, the operation electrical energy can be transmitted to the power line V2, the sensor 311, the driving unit 312, the control unit 313 and the network unit 314 through the power line V1 and the controlled switch SW1. Therefore, the control unit 313 of the target module $SM_1$ is powered to function after the controlled switch SW1 is turned on, and completes preparing and outputs the initialization packet $INI_1$ during the second period P2 after the first period P1 is ended, as that shown in FIG. 6. After the control unit 313 of the target module $SM_1$ outputs the initialization packet $INI_1$, the control unit 313 turns on the controlled switch SW2 in the power delay circuit 820 of the target module $SM_2$. Therefore, a sensing unit 810 in the target module $SM_2$ can obtain the operation electrical energy through the power line V2 and the controlled switch SW2 after the second period P2 is ended, and outputs the initialization packet $INI_2$ during the third period P3, as that shown in FIG. 6.

Here, a method for initializing the control system of the aforementioned embodiments is described below. The control system includes n target modules $SM_1$-$SM_n$, and the target modules $SM_1$-$SM_n$ respectively have at least a data transmission end, at least a power input end and at least a power output end, wherein n is an integer. The method for initializing the control system includes following steps. An operation electrical energy is supplied to the power input end of the target module $SM_1$. The operation electrical energy is delayed by the first period P1 by the target module $SM_1$, and is output via the power output end of the target module $SM_1$. The operation electrical energy output from the power output end of the target module $SM_{(i-1)}$ is received by the power input end of the other target module $SM_i$, where i is an integer, and $1 \le i \le n$. The operation electrical energy is delayed by an $i^{th}$ period by the target module $SM_i$, and is output via the power output end of the target module $SM_i$.

Figure 9A:
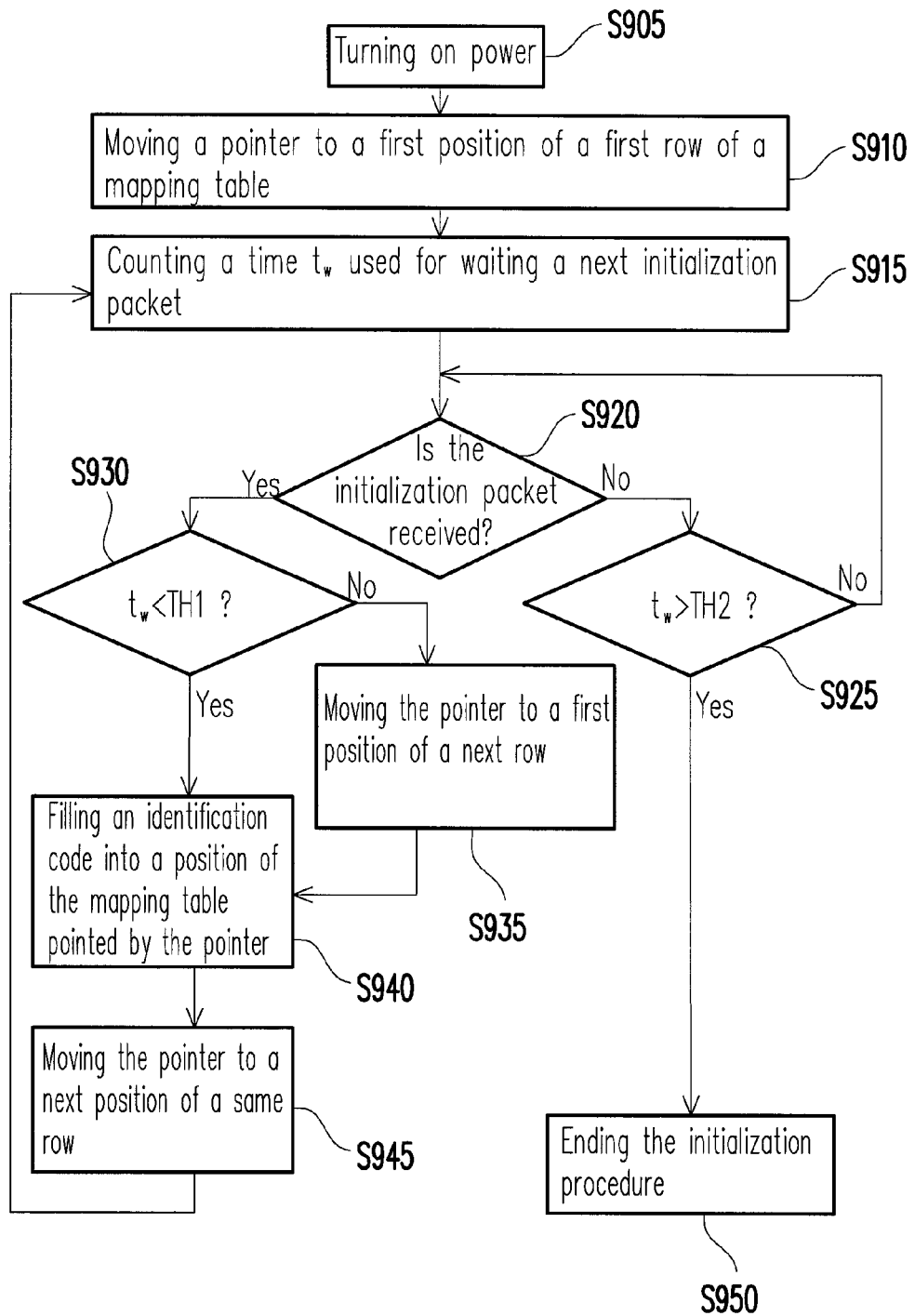
FIG. 9A is a flowchart illustrating a method for initializing a control platform according to an exemplary embodiment of the disclosure.

FIG. 9A is a flowchart illustrating a method for initializing the control platform 110 according to an exemplary embodiment of the disclosure. When the power is turned on (step S905), the control platform 110 is initialized, and the operation electrical energy is transmitted to the power line V1. During the initializing process, the control platform 110 establishes a mapping table, and moves a pointer to an initial position of the mapping table, for example, a first position of a first row (step S910). Then, the control platform 110 waits to receive packets from the data transmission line DL, for example, the initialization packets and sensing data packets transmitted back by the target modules $SM_1$-$SM_n$. In step S915, the control platform 110 counts a message waiting time $t_w$ waited for receiving a next initialization packet. Then, in step S920, the control platform 110 determines whether an initialization packet is received. During a period that the next initialization packet is not received, the control platform 110 continually counts the message waiting time $t_w$, and compares the message waiting time $t_w$ with a second threshold TH2 (step S925). If the message waiting time $t_w$ exceeds the second threshold TH2, the control platform 110 ends the initialization procedure (step S950). If the message waiting time $t_w$ is smaller than the second threshold TH2, the control platform 110 returns back to the step S920 to wait a next initialization packet.

When the message waiting time $t_w$ does not reach the second threshold TH2, and the control platform 110 receives the next initialization packet, a step S930 is executed, by which the control platform 110 compares whether the message waiting time $t_w$ exceeds a first threshold TH1. The first threshold TH1 is smaller than the second threshold TH2, and the two thresholds TH1 and TH2 are determined according to an actual product design requirement. If the message waiting time $t_w$ is smaller than the first threshold TH1, the control platform 110 fills the identification code (or other identification information) in the currently received initialization packet into the mapping table at a position currently pointed by the pointer (step S940). If the message waiting time $t_w$ is greater than the first threshold TH1, the control platform 110 moves the pointer of the mapping table to a first position of a next row (step S935), and fills the identification code of the currently received initialization packet into the mapping table at the new position pointed by the pointer (step S940). After the step S940 is completed, the control platform 110 moves the pointer of the mapping table to a next position of the same row (step S945), and sets the message waiting time $t_w$ to zero, and then counts the message waiting time $t_w$ of the next initialization packet (step S915).

Figure 9B:
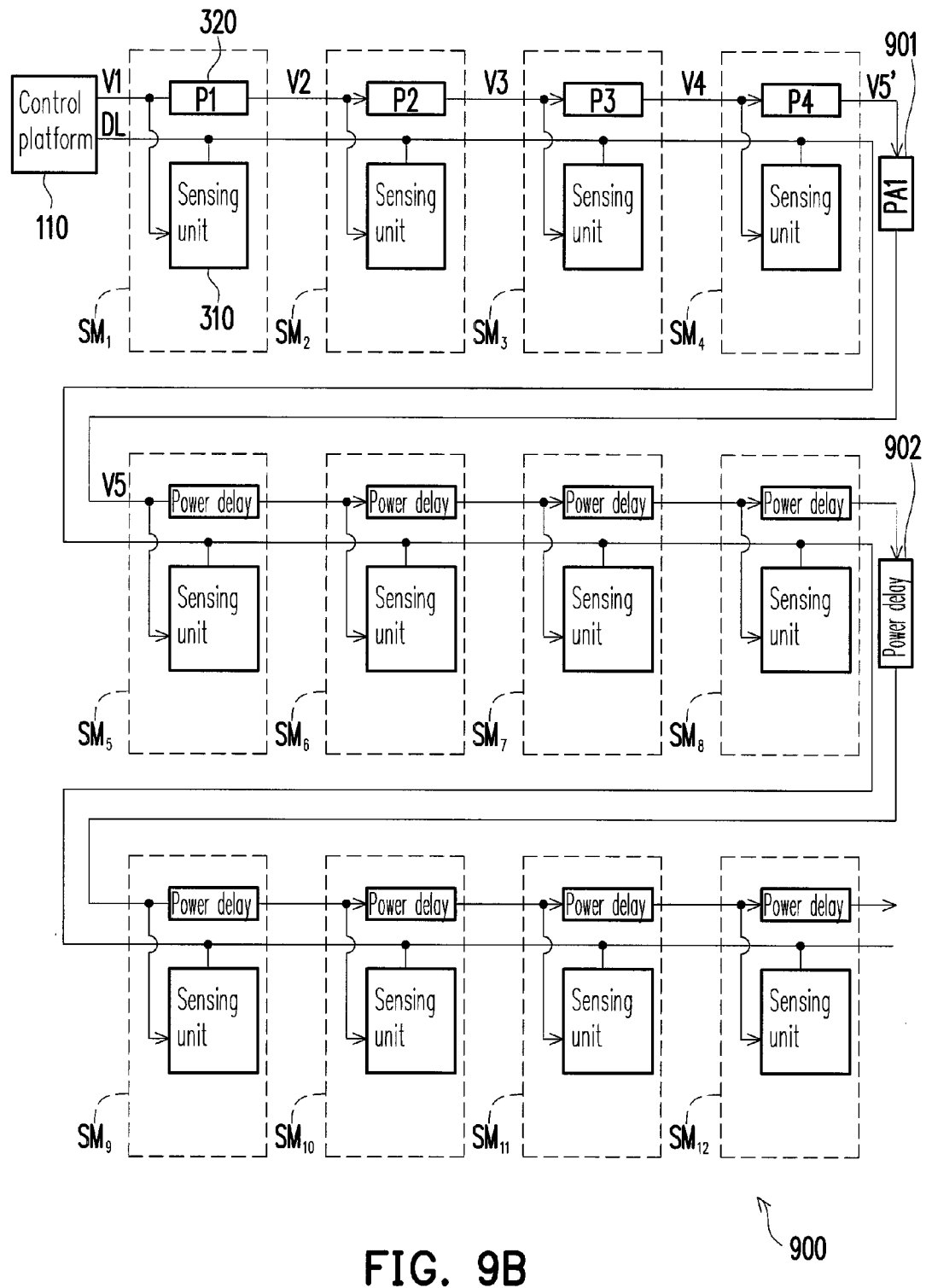
FIG. 9B is a functional block schematic diagram of a control system according to another exemplary embodiment of the disclosure.

Taking an application of the tech-care as an example, the target modules $SM_1$-$SM_n$ of FIG. 1A can be disposed on the bed or floor in any layout method according to an actual application requirement. For example, the target modules $SM_1$-$SM_n$ are disposed on the bed in a layout method of 1×n array, so that the target modules $SM_1$-$SM_n$ can be assembled as a sensing mattress with an area equivalent to a bed area. However, the target modules $SM_1$-$SM_n$ can also be disposed in the sensing environment in other layout methods. For example, FIG. 9B is a functional block schematic diagram of a control system 900 according to another exemplary embodiment of the disclosure. Related descriptions of FIG. 1A, FIG. 2 and FIG. 3 can be referred for the embodiment of FIG. 9B, and a difference between the embodiment of FIG. 1A and the embodiment of FIG. 9B lies in the layout method of the target modules $SM_1$-$SM_{12}$.

The control system 900 includes the control platform 110 and the target modules $SM_1$-$SM_{12}$, where the target modules $SM_1$-$SM_{12}$ can be assembled as a sensing mattress or a sensing mat of a 3×4 array. The layout method of the 3×4 array of FIG. 9B is only an example. Those skilled in the art can determine a number of the target modules according to a magnitude of the sensing area, and determine the layout method of the target modules according to a geometric shape of the sensing area. Related descriptions of FIG. 3 can be referred for implementation of the target modules $SM_1$-$SM_{12}$ of the present exemplary embodiment. Moreover, different to the embodiment of FIG. 1A, the control system 900 of FIG. 9B further includes a power delay circuit 901 and a power delay circuit 902. Implementations of the power delay circuit 901 and the power delay circuit 902 are similar to that of the power delay circuit 320 of the aforementioned embodiments.

Figures 9C, 10:
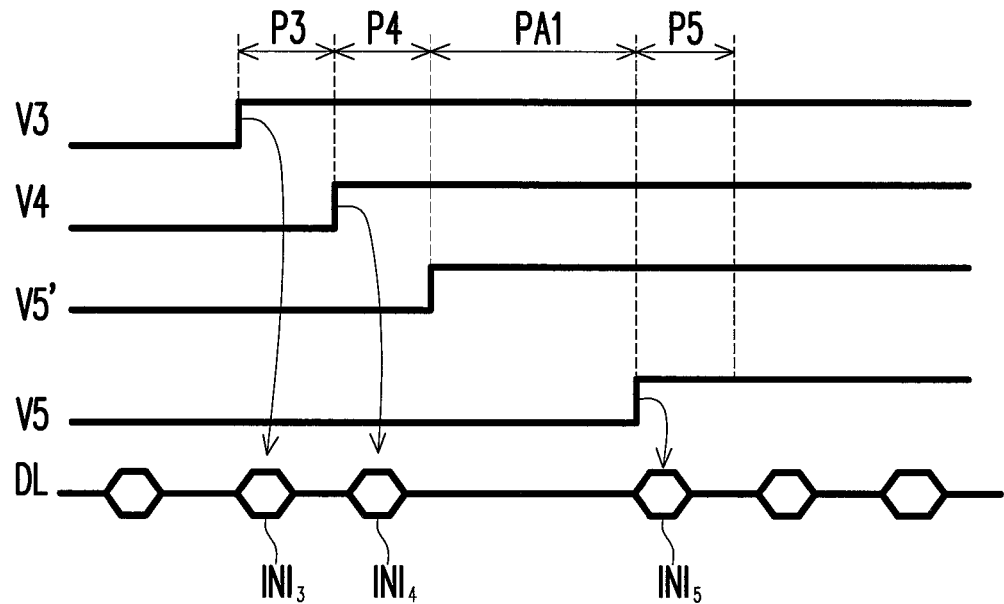
FIG. 9C is a schematic diagram illustrating a mapping table of a control platform of FIG. 9B according to an exemplary embodiment of the disclosure.
FIG. 10 is a signal timing diagram of the control system of FIG. 9B according to an exemplary embodiment of the disclosure.

Referring to FIG. 9A and FIG. 9B, the target modules $SM_1$-$SM_3$ respectively transmit the initialization packets $INI_1$-$INI_3$ to the control platform 110 during the periods P1-P3. The control platform 110 establishes the mapping table after being booted, and moves the pointer to the initial position of the mapping table, for example, a first position of a first row (the step S910). If the message waiting time $t_w$ (a time period from when the control platform 110 is booted till the initialization packet $INI_1$ is received) is smaller than the first threshold TH1, the step S940 is executed, by which the control platform 110 fills the identification code of the initialization packet $INI_1$ of the target module $SM_1$ into the mapping table at a position pointed by the pointer, as that shown in FIG. 9C. FIG. 9C is a schematic diagram illustrating a mapping table of the control platform 110 of FIG. 9B according to an exemplary embodiment of the disclosure. In FIG. 9C, $SM_1$-$SM_{12}$ respectively represent the identification codes of the target modules $SM_1$-$SM_{12}$. After the step S940 is completed, the control platform 110 moves the pointer of the mapping table to a second position of the same row (the step S945), and sets the message waiting time $t_w$ to zero, and then counts the message waiting time $t_w$ of the next initialization packet $INI_2$ (step S915).

After the initialization packet $INI_1$ is received, if the message waiting time $t_w$ that the control platform 110 waits for the next initialization packet $INI_2$ is smaller than the first threshold value TH1, the step S940 is executed, by which the control platform 110 fills the identification code of the initialization packet $INI_2$ of the target module $SM_2$ into the mapping table at a position pointed by the pointer, as that shown in FIG. 9C. After the step S940 is completed, the control platform 110 moves the pointer of the mapping table to a third position of the same row (the step S945), and sets the message waiting time $t_w$ to zero, and then counts the message waiting time $t_w$ of the next initialization packet $INI_3$ (step S915).

FIG. 10 is a signal timing diagram of the control system 900 of FIG. 9B according to an exemplary embodiment of the disclosure. Referring to FIG. 9B and FIG. 10, the power input end of the target module $SM_3$ receives the operation electrical energy through the power line V3, and the operation electrical energy is delayed by the third period P3 and is output to the power line V4 through the power output end of the target module $SM_3$. The operation electrical energy is supplied to the sensing unit of the target module $SM_3$ for the sensing operation. During an initial stage (the third period P3) that the power input end of the target module $SM_3$ receives the operation electrical energy, the sensing unit of the target module $SM_3$ transmits the initialization packet $INI_3$ to the control platform 110 through the data transmission end and the data transmission line DL.

After the initialization packet $INI_2$ is received, if the message waiting time $t_w$ that the control platform 110 waits for the next initialization packet $INI_3$ is smaller than the first threshold value TH1, the step S940 is executed, by which the control platform 110 fills the identification code of the initialization packet $INI_3$ of the target module $SM_3$ into the mapping table at a position pointed by the pointer, as that shown in FIG. 9C. After the step S940 is completed, the control platform 110 moves the pointer of the mapping table to a fourth position of the same row (the step S945), and sets the message waiting time $t_w$ to zero, and then counts the message waiting time $t_w$ of the next initialization packet $INI_4$ (step S915).

The power input end of the target module $SM_4$ receives the operation electrical energy through the power line V4, and the operation electrical energy is delayed by a fourth period P4 and is output to a power line V5' through the power output end of the target module $SM_4$. During an initial stage (the fourth period P4) that the power input end of the target module $SM_4$ receives the operation electrical energy, the sensing unit of the target module $SM_4$ transmits the initialization packet $INI_4$ to the control platform 110 through the data transmission end and the data transmission line DL.

After the initialization packet $INI_3$ is received, if the message waiting time $t_w$ that the control platform 110 waits for the next initialization packet $INI_4$ is smaller than the first threshold value TH1, the step S940 is executed, by which the control platform 110 fills the identification code of the initialization packet $INI_4$ of the target module $SM_4$ into the mapping table at a position pointed by the pointer, as that shown in FIG. 9C. After the step S940 is completed, the control platform 110 moves the pointer of the mapping table to a fifth position of the same row (the step S945), and sets the message waiting time $t_w$ to zero, and then counts the message waiting time $t_{wi}$ of the next initialization packet $INI_5$ (step S915).

Since the target module $SM_4$ is the last target module in the first row of the 3×4 array, the power delay circuit 901 is disposed between the target module $SM_4$ and the target module $SM_5$. The power delay circuit 901 receives the operation electrical energy through the power line V5', and delays the operation electrical energy by a period PA1, and then outputs it to a power line V5. The power input end of the target module $SM_5$ receives the operation electrical energy through the power line V5. During an initial stage (the fifth period P5) that the power input end of the target module $SM_5$ receives the operation electrical energy, the sensing unit of the target module $SM_5$ transmits an initialization packet $INI_5$ to the control platform 110 through the data transmission end and the data transmission line DL. Here, the message waiting time $t_w$ is defined as a time period from when the target module $SM_{(i-1)}$ outputs the initialization packet $INI_{(i-1)}$ to the control platform 110 to the time when the target module $SM_i$ outputs the initialization packet $INI_i$ to the control platform 110. According to FIG. 10, it is known that the message waiting time $t_w$ between the initialization packet $INI_3$ and the initialization packet $INI_4$ is different to the message waiting time $t_w$ between the initialization packet $INI_4$ and the initialization packet $INI_5$.

After the initialization packet $INI_4$ is received, if the message waiting time $t_w$ that the control platform 110 waits for the next initialization packet $INI_5$ is greater than the first threshold value TH1, the step S935 is executed, by which the control platform 110 moves the pointer of the mapping table to a first position of a next row, which is the first position of the second row in the present exemplary embodiment. Then, the step S940 is executed, by which the control platform 110 fills the identification code of the initialization packet $INI_5$ of the target module $SM_5$ into the mapping table at a position pointed by the pointer, as that shown in FIG. 9C. After the step S940 is completed, the control platform 110 moves the pointer of the mapping table to a next position of the same row (the step S945), and sets the message waiting time $t_w$ to zero, and then counts the message waiting time $t_w$ of the next initialization packet $INI_4$ (step S915).

Namely, if the message waiting time $t_w$ between the initialization packet $INI_{(i-1)}$ and the initialization packet $INI_i$ is smaller than the first threshold TH1, the control platform 110 sets the target module $SM_{(i-1)}$ and the target module $SM_i$ to be in the same row in the layout of the target modules $SM_1$-$SM_n$. If the message waiting time $t_w$ between the initialization packet $INI_{(i-1)}$ and the initialization packet $INI_i$ is greater than the first threshold TH1 and is smaller than the second threshold TH2, the control platform 110 sets the target module $SM_{(i-1)}$ and the target module $SM_i$ to be in different rows in the layout of the target modules $SM_1$-$SM_n$.

Taking the embodiment of FIG. 9B as an example, it is assumed that the delay time of the power delay circuits (for example, the power delay circuit 320) of the target modules $SM_1$-$SM_n$ are approximately the same. During a process that the control platform 110 sequentially receives the initialization packets $INI_1$-$INI_4$, the control platform 110 counts the message waiting time $t_w$ of the initialization packets $INI_1$-$INI_4$. Since the message waiting time $t_w$ of the initialization packets $INI_1$-$INI_4$ are all smaller than the first threshold TH1, the control platform 110 sets/positions the target modules $SM_1$-$SM_4$ to be in the same row (the first row) of the 3×4 array. According to a sequence that the control platform 110 receives the initialization packets $INI_1$-$INI_4$, the control platform 110 sequentially records the identification codes of the target modules $SM_1$-$SM_4$ at the first to the fourth positions of the first row of the "sensing array mapping table", as that shown in FIG. 9C. After the initialization packet $INI_4$ is received, if the message waiting time $t_w$ that the control platform 110 waits for the initialization packet $INI_5$ is greater than the first threshold TH1 and is smaller than the second threshold TH2, the control platform 110 sets the target module $SM_4$ and the target module $SM_5$ to be in different rows of the 3×4 array.

Then, deduced by analogy, the control platform 110 can sequentially set/position the target modules $SM_5$-$SM_8$ to be in the same row (the second row) of the 3×4 array, and record the identification codes of the target modules $SM_5$-$SM_8$ to the first position to the fourth position of the second row of the "sensing array mapping table", as that shown in FIG. 9C. Due to the time delay of the power delay circuit 902, the control platform 110 can set/position the target module $SM_8$ and the target module $SM_9$ to be in different rows of the 3×4 array. Then, the control platform 110 can sequentially set/position the target modules $SM_9$-$SM_{12}$ to be in the same row (the third row) of the 3×4 array, and record the identification codes of the target modules $SM_9$-$SM_{12}$ to the first position to the fourth position of the third row of the "sensing array mapping table", as that shown in FIG. 9C. After the step S925, if it is found that the message waiting time $t_w$ (a time period for waiting a next initialization packet after the control platform 110 receives the initialization packet $INI_{12}$ of the target module $SM_{12}$) is greater than the second threshold TH2, the control platform 110 sets/positions the target module $SM_{12}$ as a last target module in the layout of the target modules $SM_1$-$SM_{12}$, and ends the above setting/positioning procedure (the initialization procedure).

Therefore, after the initialization procedure is completed, the control platform 110 can obtain and record the layout positions of the target modules $SM_1$-$SM_n$ according to a time sequence that the target modules $SM_1$-$SM_n$ output the initialization packets $INI_1$-$INI_n$ and the message waiting time $t_w$. In case of a normal operation, the target modules $SM_1$-$SM_{12}$ regularly or irregularly transmit data packets including sensing results and identification codes to the control platform 110 through the data transmission line DL. After the control platform 110 receives the data packet, the control platform 110 can determine a position of the target module in the 3×4 array where the data packet is sent according to the aforementioned sensing array mapping table.

Figure 11:
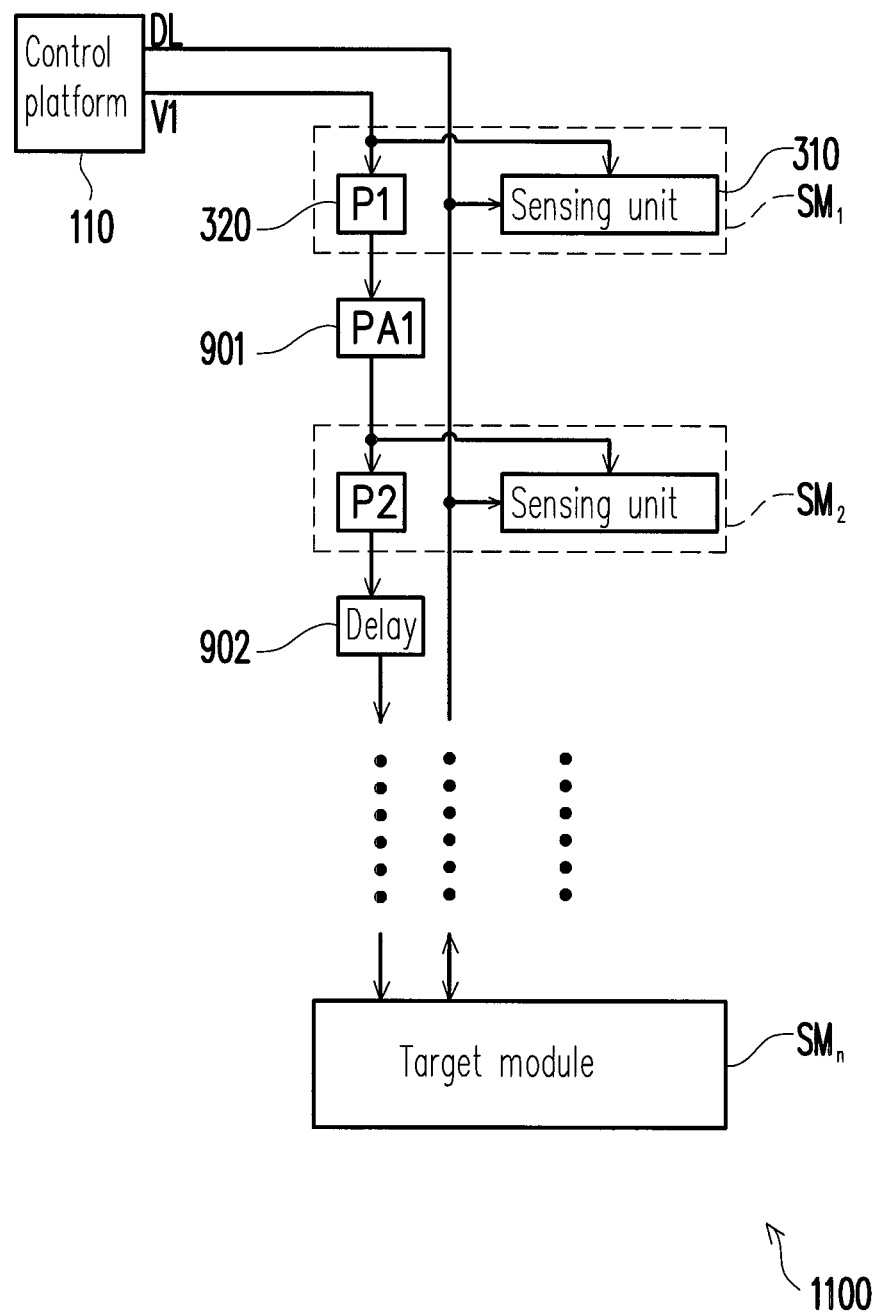
FIG. 11 is a functional block schematic diagram of a control system according to still another exemplary embodiment of the disclosure.

FIG. 11 is a functional block schematic diagram of a control system 1100 according to still another exemplary embodiment of the disclosure. Related descriptions of the embodiments of FIG. 1A, FIG. 2, FIG. 3, FIG. 9B and FIG. 10 can be referred for the embodiment of FIG. 11. Different to the embodiment of FIG. 9B, the layout method of the target modules $SM_1$-$SM_n$ of FIG. 11 is an n×1 array. The control platform 110 first receives the initialization packet $INI_1$ of the target module $SM_1$, so that the target module $SM_1$ is set/positioned at the first position of the first row in the n×1 array, and then the identification code of the target module $SM_1$ is recorded to the first position of the first row of the "sensing array mapping table". Due to the time delay of the power delay circuit 901, the "message waiting time" that the control platform 110 waits for the initialization packet $INI_2$ after the control platform 110 receives the initialization packet $INI_1$ is greater than the first threshold and smaller than the second threshold TH2. Namely, the target module $SM_1$ and the target module $SM_2$ are respectively belonged to different rows of the n×1 array. Therefore, the control platform 110 can set/position the target module $SM_2$ at the first position of the second row of the n×1 array, and then record the identification code of the target module $SM_2$ to the first position of the second row of the "sensing array mapping table". Deduced by analogy, the control platform 110 can set/position the target module $SM_n$ at the first position of the $n^{th}$ row of the n×1 array, and then record the identification code of the target module $SM_n$ to the first position of the $n^{th}$ row of the "sensing array mapping table". If the message waiting time $t_w$ that the control platform 110 waits for the next initialization packet $INI_2$ is smaller than the first threshold value TH1, if a time period for waiting a next initialization packet after the control platform 110 receives the initialization packet of the target module $SM_n$ is greater than the second threshold TH2, the control platform 110 sets/positions the target module $SM_n$ as a last target module in the layout of the target modules $SM_1$-$SM_{12}$, and ends the above setting/positioning procedure.

Figure 12:
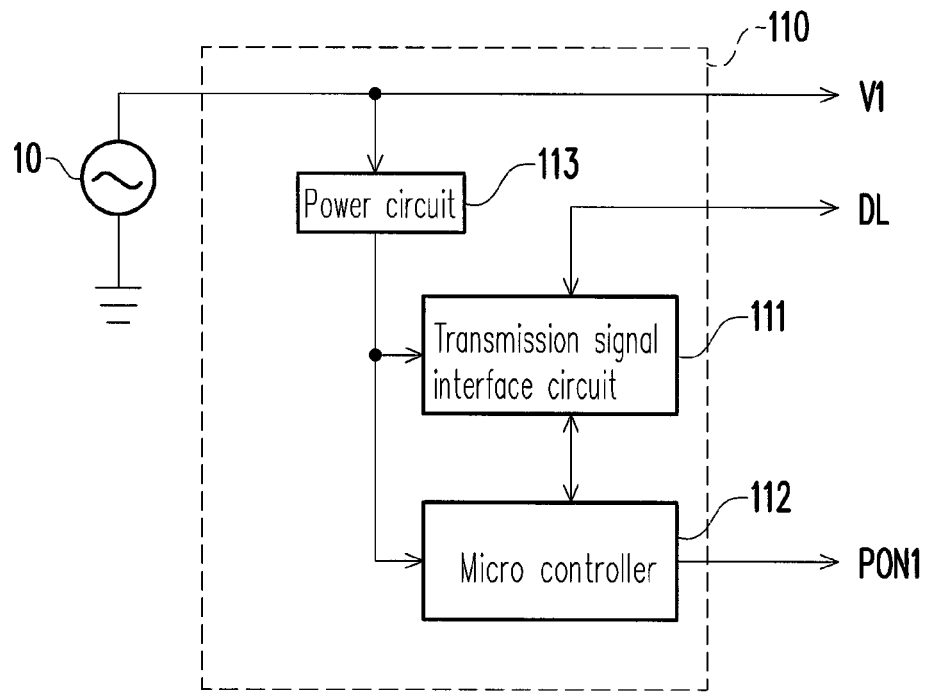
FIG. 12 is a functional block schematic diagram of the control platform of FIG. 1A according to another exemplary embodiment of the disclosure.

FIG. 12 is a functional block schematic diagram of the control platform 110 of FIG. 1A according to another exemplary embodiment of the disclosure. Related descriptions of the embodiment of FIG. 1B can be referred for the control platform 110 of FIG. 12. Different to the control platform 110 of FIG. 1B, the micro controller 112 of the control platform 110 of FIG. 12 may further output a power enable signal PON1 to the target module SM$_1$ to control the power delay circuit 320 in the target module SM$_1$.

The target modules SM$_1$-SM$_n$ respectively have at least a data transmission end D, at least a power input end Pin, at least a power output end Pout, at least a power enable end Pon and at least a power control end. In the present exemplary embodiment, the target modules SM$_1$-SM$_n$ respectively have two power control ends PC1 and PC2. The data transmission ends D of the target modules SM$_1$-SM$_n$ are electrically connected to the control platform 110 through the data transmission line DL. It is determined whether or not to activate each of the target modules SM$_i$ according to control of the power enable end Pon, and after the target modules SM$_i$ is activated for an i$^{th}$ period, a power enable signal PONi is output from the power control end (PC1 or PC2).

Figure 13:
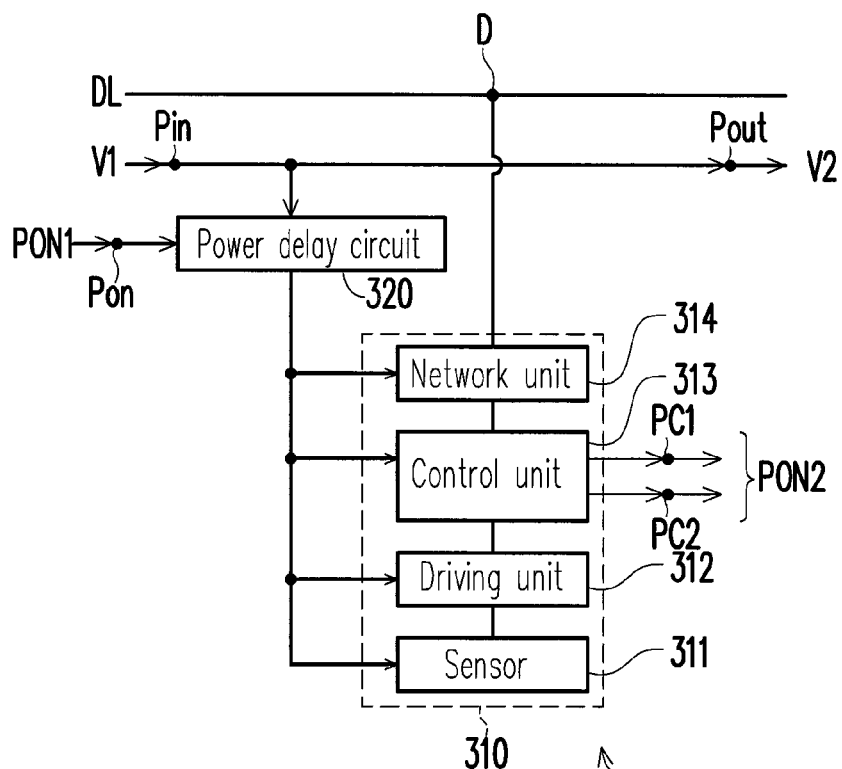
FIG. 13 is an internal functional block schematic diagram of the target module $SM_1$ of FIG. 1A according to an exemplary embodiment of the disclosure.

FIG. 13 is an internal functional block schematic diagram of the target module SM$_1$ of FIG. 1A according to an exemplary embodiment of the disclosure. Implementations of the other target modules SM$_2$-SM$_n$ can be deduced according to related descriptions of the target module SM$_1$ of FIG. 13. The power input end Pin of the target module SM$_1$ receives the operation electrical energy through the power line V1. The power output end Pout of the target module SM$_1$ outputs the operation electrical energy to the power input end Pin of the next target module SM$_2$ through the power line V2. The power enable end Pon of the target module SM$_1$ is electrically connected to the control platform 110 for receiving the power enable signal PON1.

The power input end Pin of the target module SM$_i$ receives the operation electrical energy provided by the power output end Pout of the target module SM$_{(i-1)}$ of the previous stage. The power output end Pout of the target module SM$_i$ outputs the operation electrical energy to the next target module SM$_{(i+1)}$. The power enable end Pon of the target module SM$_i$ is electrically connected to one of the power control ends PC1 and PC2 of the target module SM$_{(i-1)}$ of the previous stage for receiving the power enable signal PONi.

Related descriptions of the target module SM$_1$ of FIG. 3 can be referred for the target module SM$_1$ of FIG. 13, and a difference there between is that the input end of the power delay circuit 320 of the target module SM$_1$ of FIG. 13 is connected to the power input end Pin and the power output end Pout of the target module SM$_1$ for receiving the operation electrical energy. The control end of the power delay circuit 320 is connected to the power enable end Pon of the target module SM$_1$ for receiving the power enable signal PON1. The power delay circuit 320 determines whether or not to supply the operation electrical energy to the sensing unit 310 through the output end thereof under control of the power enable signal PON1.

During the initial stage that the control unit 313 of the sensing unit 310 is powered, it prepares the initialization packet INI$_1$, and transmits the initialization packet INI$_1$ to the control platform 110 through the network unit 314 and the data transmission line DL. After the first period P1, the control unit 313 has transmitted the initialization packet INI$_1$ to the control platform 110, and now the control unit 313 outputs a power enable signal PON2 to the power enable end Pon of the next target module SM$_2$ through one of the power control ends PC1 and PC2. The power control ends PC1 and PC2 have different delay time te1 and te2. By selecting to connect the power control end PC1 or PC2 to the power enable end Pon of the next target module SM$_2$, a time length of the first period P1 is determined.

Figure 14A:
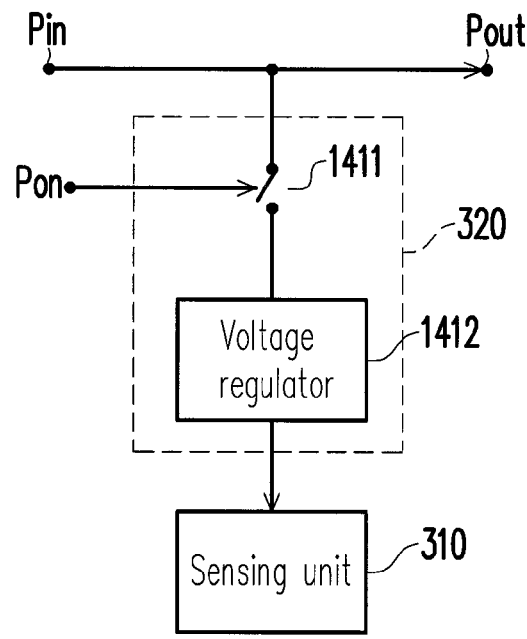
FIG. 14A is a functional block schematic diagram of a power delay circuit of FIG. 13 according to an exemplary embodiment of the disclosure.

Implementation of the power delay circuit 320 is not limited by the disclosure. For example, FIG. 14A is a functional block schematic diagram of the power delay circuit 320 of FIG. 13 according to an exemplary embodiment of the disclosure. Referring to FIG. 14A, the power delay circuit 320 includes a switch 1411 and a voltage regulator 1412. A first end of the switch 1411 is connected to the power input end Pin and the power output end Pout of the target module SM$_1$, and a second end of the switch 1411 is connected to an input end of the voltage regulator 1412. An output end of the voltage regulator 1412 is connected to a power end of the sensing unit 310. A control end of the switch 1411 is connected to the power enable end Pon of the target module SM$_1$. The switch 1411 is turned on or turned off under control of the power enable end Pon. Therefore, the power delay circuit 320 determines whether or not to supply the operation electrical energy to the sensing unit 310 under control of the power enable end Pon.

Figure 14B:
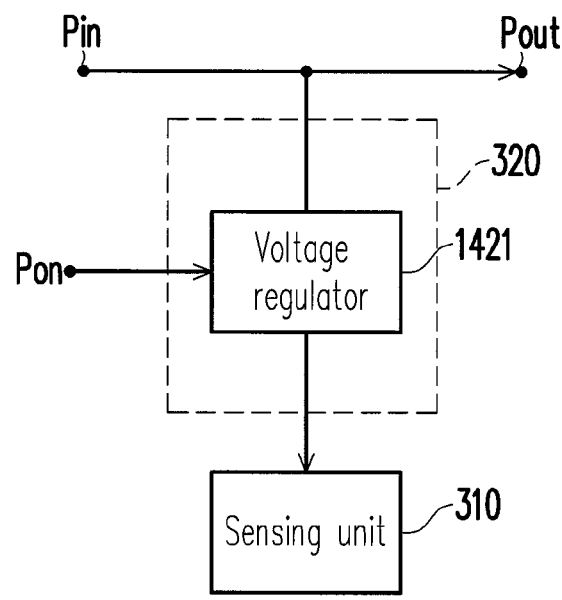
FIG. 14B is a functional block schematic diagram of a power delay circuit of FIG. 13 according to another exemplary embodiment of the disclosure.

FIG. 14B is a functional block schematic diagram of the power delay circuit 320 of FIG. 13 according to another exemplary embodiment of the disclosure. Referring to FIG. 14B, the power delay circuit 320 includes a voltage regulator 1421 capable of being enabled. An input end of the voltage regulator 1421 is connected to the power input end Pin and the power output end Pout of the target module SM$_1$, and an output end of the voltage regulator 1421 is connected to the power end of the sensing unit 310. An enable end of the voltage regulator 1421 is connected to the power enable end Pon of the target module SM$_1$. The voltage regulator 1421 is enabled or disabled under control of the power enable end Pon. Therefore, the power delay circuit 320 determines whether or not to supply the operation electrical energy to the sensing unit 310 under control of the power enable end Pon.

Figure 15:
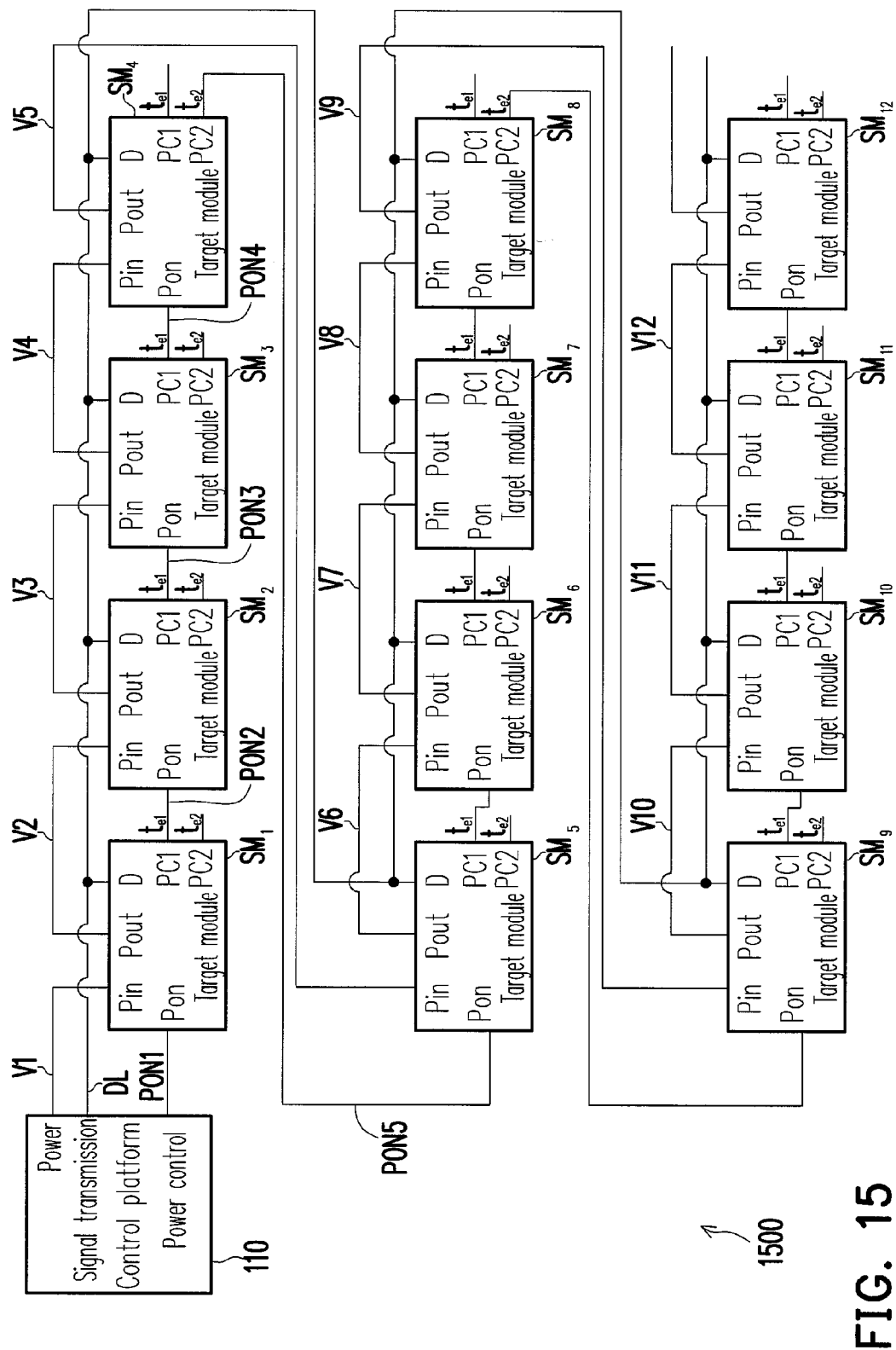
FIG. 15 is a functional block schematic diagram of a control system according to another exemplary embodiment of the disclosure.

FIG. 15 is a functional block schematic diagram of a control system 1500 according to another exemplary embodiment of the disclosure. Related descriptions of FIG. 1A, FIG. 2, FIG. 12 and FIG. 13 can be referred for implementation of the control system 1500 of FIG. 15. The control system 1500 includes a control platform 110 and target modules SM$_1$-SM$_{12}$, where the target modules SM$_1$-SM$_{12}$ can be assembled as a sensing mattress or a sensing mat of a 3×4 array. The layout method of the 3×4 array of FIG. 15 is only an example. Those skilled in the art can determine a number of the target modules according to a magnitude of the sensing area, and determine the layout method of the target modules according to a geometric shape of the sensing area. Related descriptions of FIG. 13 can be referred for implementations of the target modules SM$_1$-SM$_{12}$ of the present exemplary embodiment, and related descriptions of FIG. 9A and FIG. 12 can be referred for implementation of the control platform 110.

Figure 16:
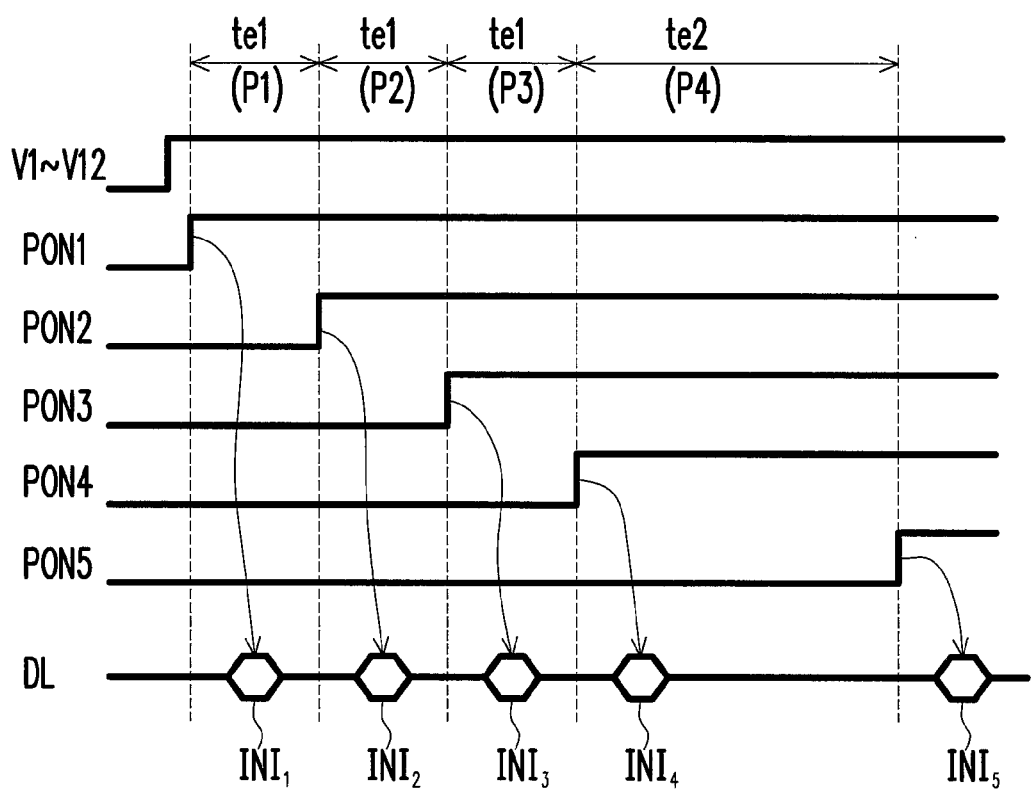
FIG. 16 is a signal timing diagram of the control system of FIG. 15 according to an exemplary embodiment of the disclosure.

FIG. 16 is a signal timing diagram of the control system 1500 of FIG. 15 according to an exemplary embodiment of the disclosure. Referring to FIG. 15 and FIG. 16, after the power supply 10 supplies power to the control platform 110, the control platform 110 transmits the operation electrical energy to the target modules SM$_1$-SM$_{12}$ through the power lines V1-V12, as that shown in FIG. 16. After the power supply 10 supplies power to the control platform 110, the micro controller 112 of the control platform 110 transmits the power enable signal PON1 to the target module SM$_1$. The power delay circuit 320 of the target module SM$_1$ determines to supply the operation electrical energy to the sensing unit 310 of the target module SM$_1$ under control of the power enable signal PON1. During an initial stage (the first period P1) that the control unit 313 of the sensing unit 310 is powered, the control unit 313 transmits the initialization packet INI$_1$ to the control platform 110 through the data transmission line DL, as that shown in FIG. 16. After the delay time te1 (the first period P1), the control unit 313 outputs the power enable signal PON2 to the power enable end Pon of the next target module $SM_2$ through the power control end PC1. Deduced by analogy, the target modules $SM_2$-$SM_4$ respectively transmit the initialization packets $INI_2$-$INI_4$ to the control platform 110 after receiving the power enable signals PON2-PON4.

The control platform 110 establishes a mapping table after being booted, and moves a pointer to an initial position of the mapping table, for example, a first position of a first row (step S910). If the message waiting time $t_w$ (a time period from when the control platform 110 is booted till the initialization packet $INI_1$ is received, which is about the delay time te1) is smaller than the first threshold TH1, the control platform 110 fills the identification code of the initialization packet $INI_1$ of the target module $SM_1$ into the mapping table at a position pointed by the pointer. After recording of the initialization packet $INI_1$ is completed, the control platform 110 moves the pointer of the mapping table to a second position of the same row, and sets the message waiting time $t_w$ to zero, and then counts the message waiting time $t_w$ of the next initialization packet $INI_2$.

After the initialization packet $INI_1$ is received, if the message waiting time $t_w$ (which is about the delay time te1) that the control platform 110 waits for the next initialization packet $INI_2$ is smaller than the first threshold value TH1, the control platform 110 fills the identification code of the initialization packet $INI_2$ of the target module $SM_2$ into the mapping table at the second position of the first row pointed by the pointer. Then, the control platform 110 moves the pointer of the mapping table to a third position of the same row, and sets the message waiting time $t_w$ to zero, and then counts the message waiting time $t_w$ of the next initialization packet $INI_3$.

After the initialization packet $INI_2$ is received, if the message waiting time $t_w$ (which is about the delay time te1) that the control platform 110 waits for the next initialization packet $INI_3$ is smaller than the first threshold value TH1, the control platform 110 fills the identification code of the initialization packet $INI_3$ of the target module $SM_3$ into the mapping table at the third position of the first row pointed by the pointer. Then, the control platform 110 moves the pointer of the mapping table to a fourth position of the same row, and sets the message waiting time $t_w$ to zero, and then counts the message waiting time $t_w$ of the next initialization packet $INI_4$.

During an initial stage that the target module $SM_4$ is powered, the target module $SM_4$ transmits the initialization packet $INI_4$ to the control platform 110 through the data transmission line DL, as that shown in FIG. 16. If the message waiting time $t_w$ (which is about the delay time te1) that the control platform 110 waits for the initialization packet $INI_4$ is smaller than the first threshold value TH1, the control platform 110 fills the identification code of the initialization packet $INI_4$ of the target module $SM_4$ into the mapping table at the fourth position of the first row pointed by the pointer. Then, the control platform 110 moves the pointer of the mapping table to a fifth position of the same row, and sets the message waiting time $t_w$ to zero, and then counts the message waiting time $t_w$ of the next initialization packet $INI_5$.

Here, the power control end PC2 of the target module $SM_4$ is connected to the power enable end Pon of to next target module $SM_5$. Since the delay time te2 of the power control end PC2 is greater than the delay time te1 of the power control end PC1, after the delay time te2 (the fourth period P4), the target module $SM_4$ outputs the power enable signal PON5 to the power enable end Pon of the next target module $SM_5$ through the power control end PC2. During an initial stage that the target module $SM_5$ is powered, the target module $SM_5$ transmits the initialization packet $INI_5$ to the control platform 110 through the data transmission line DL, as that shown in FIG. 16. If the message waiting time $t_w$ (which is about the delay time te2) that the control platform 110 waits for the initialization packet $INI_5$ is greater than the first threshold value TH1, the control platform 110 moves the pointer of the mapping table to a first position of a next row. Then, the control platform 110 fills the identification code of the initialization packet $INI_5$ of the target module $SM_5$ into the mapping table at the first position of the second row pointed by the pointer. Then, the control platform 110 moves the pointer of the mapping table to a next position of the same row, i.e. the second position of the second row, and sets the message waiting time $t_w$ to zero, and then counts the message waiting time $t_w$ of the next initialization packet.

Deduced by analogy, the control platform 110 can sequentially set/position the positions of the target modules $SM_5$-$SM_8$ in the same row (the second row) of the 3×4 array, and then sequentially records the identification codes of the target modules $SM_5$-$SM_8$ at the first to the fourth positions of the second row of the "sensing array mapping table". The control platform 110 can sequentially set/position the positions of the target modules $SM_9$-$SM_{12}$ in the same row (the third row) of the 3×4 array, and then sequentially records the identification codes of the target modules $SM_9$-$SM_{12}$ at the first to the fourth positions of the third row of the "sensing array mapping table". After the control platform 110 receives the initialization packet of the target module $SM_{12}$, if the message waiting time $t_w$ that the control platform 110 waits for the initialization packet of the next target module is greater than the second threshold TH2, the control platform 110 sets the target module $SM_{12}$ to be the last target module in the layout of the target modules $SM_1$-$SM_{12}$, and ends the above setting/positioning procedure (the initialization procedure).

Therefore, after the initialization procedure is completed, the control platform 110 can obtain and record the layout positions of the target modules $SM_1$-$SM_n$ according to a time sequence that the target modules $SM_1$-$SM_n$ output the initialization packets $INI_1$-$INI_n$ and the message waiting time $t_w$. In case of a normal operation, the target modules $SM_1$-$SM_{12}$ regularly or irregularly transmit data packets including sensing results and identification codes to the control platform 110 through the data transmission line DL. After the control platform 110 receives the data packet, the control platform 110 can determine a position of the target module in the 3×4 array where the data packet is sent according to the aforementioned sensing array mapping table.

Figure 17:
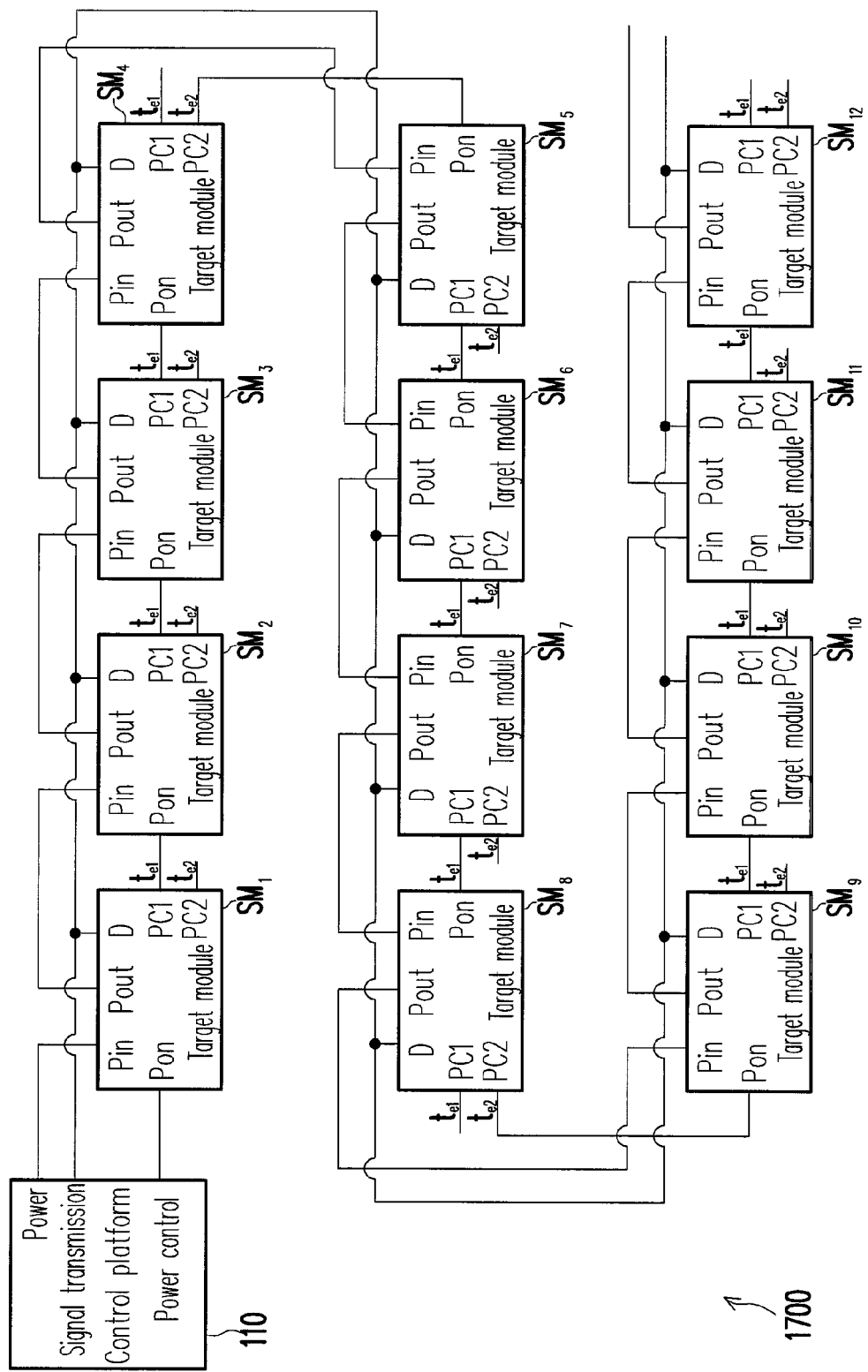
FIG. 17 is a schematic diagram illustrating a layout method of target modules $SM_1$-$SM_n$ according to still another exemplary embodiment of the disclosure.

The layout method of the target modules $SM_1$-$SM_n$ is not limited by the disclosure. For example, FIG. 17 is a schematic diagram illustrating a layout method of the target modules $SM_1$-$SM_n$ according to still another exemplary embodiment of the disclosure. Related descriptions of FIG. 15 can be referred for a control system 1700 of FIG. 17. According to a design specification of the product, the target modules $SM_1$-$SM_n$ of the control system 1700 are assembled as sensing areas of different sizes in a S-shape layout method. Therefore, the control platform 110 correspondingly changes a sequence of filling the "sensing array mapping table" according to the design specification of the product. Here, the control platform 110 can respectively record the identification codes of the target modules $SM_1$-$SM_4$ at the first, the second, the third and the fourth positions of the first row of the "sensing array mapping table" according to a time sequence. Then, the power output end PC2 of the target module $SM_4$ outputs the power enable signal PON5 to the power enable end Pon of the next target module $SM_5$. If the message waiting time $t_w$ (which is about the delay time te2) that the control platform 110 waits for the initialization packet $INI_5$ is greater than the first threshold value TH1, the control platform 110 moves the pointer of the mapping table to a corresponding position of a next row, i.e. the fourth position of the second row. Then, the control platform 110 fills the identification code of the initialization packet $INI_5$ of the target module $SM_5$ into the mapping table at the fourth position of the second row pointed by the pointer. Deduced by analogy, the control platform 110 respectively records the identification codes of the target modules $SM_5$-$SM_8$ at the fourth, the third, the second and the first positions of the second row of the "sensing array mapping table" according to a time sequence. Then, the control platform 110 sequentially records the identification codes of the target modules $SM_9$-$SM_{12}$ at the first, the second, the third and the fourth positions of the third row of the "sensing array mapping table".

Figure 18:
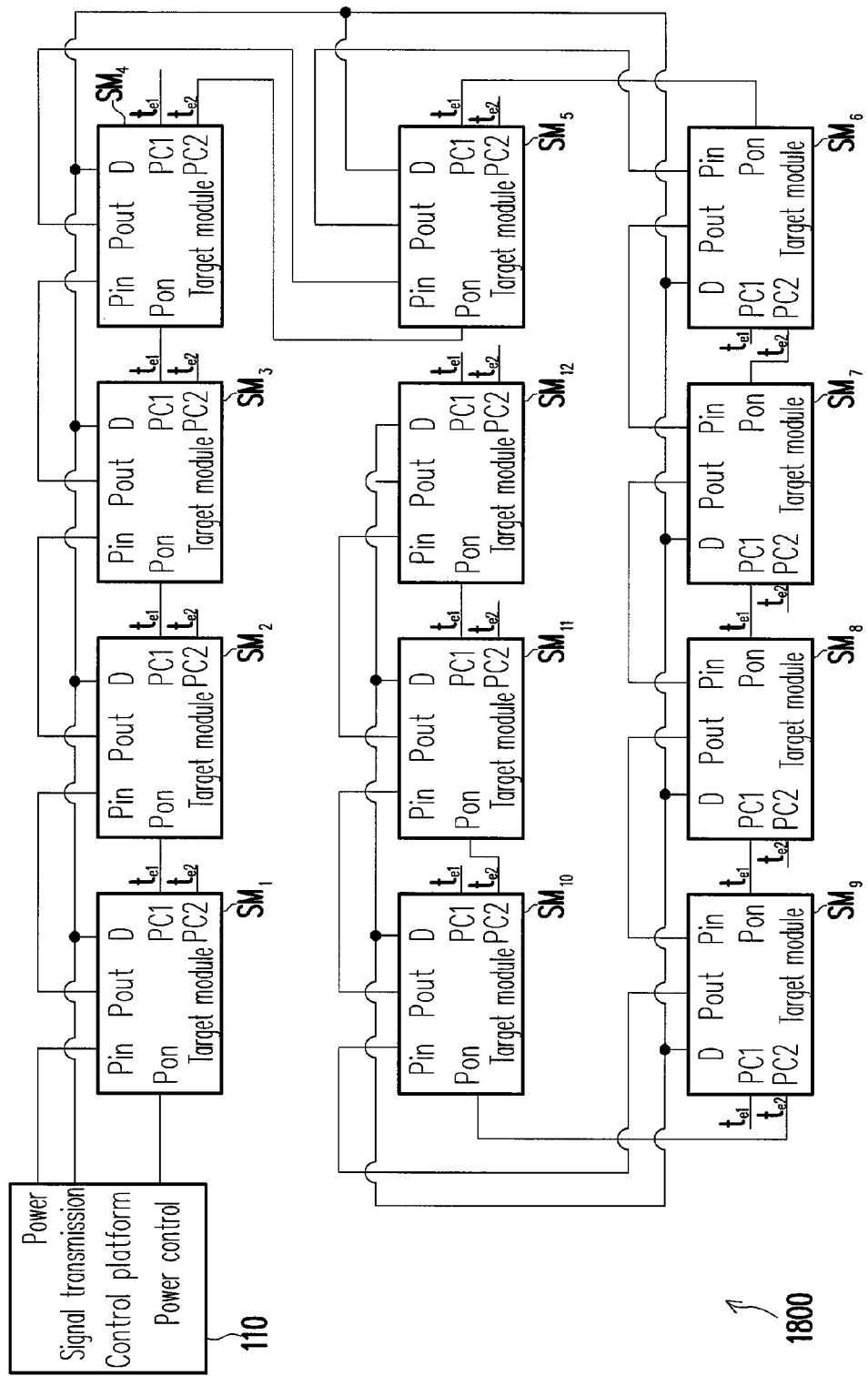
FIG. 18 is a schematic diagram illustrating a layout method of target modules $SM_1$-$SM_n$ according to yet another exemplary embodiment of the disclosure.

FIG. 18 is a schematic diagram illustrating a layout method of the target modules $SM_1$-$SM_n$ according to yet another exemplary embodiment of the disclosure. Related descriptions of FIG. 15 can be referred for a control system 1800 of FIG. 18. According to a design specification of the product, the target modules $SM_1$-$SM_n$ of the control system 1700 are assembled as sensing areas of different sizes in a circle-type layout method. Therefore, the control platform 110 correspondingly changes a sequence of filling the "sensing array mapping table" according to the design specification of the product. Here, the control platform 110 can respectively record the identification codes of the target modules $SM_1$-$SM_4$ at different positions of the first row of the "sensing array mapping table" according to a time sequence, for example, the first, the second, the third and the fourth positions of the first row.

Then, if the message waiting time $t_w$ (which is about the delay time te2) that the control platform 110 waits for the initialization packet $INI_5$ is greater than the first threshold value TH1, it represents that an arranging direction of the following target modules is changed. Therefore, the control platform 110 moves the pointer of the mapping table along a column direction, i.e. the identification codes of the following target modules are respectively recorded at different positions of the same column of the "sensing array mapping table" according to a time sequence. Therefore, the pointer of the mapping table is moved to a corresponding position of a next row, i.e. the fourth position of the second row. Then, the control platform 110 fills the identification codes of the initialization packets $INI_5$-$INI_6$ of the target modules $SM_5$-$SM_6$ into the mapping table at the fourth position of the second row and the fourth position of the third row pointed by the pointer. Deduced by analogy, the control platform 110 sequentially records the identification codes of the target modules $SM_7$-$SM_9$ at the third, the second and the first positions of the third row of the "sensing array mapping table". Then, the control platform 110 sequentially records the identification codes of the target modules $SM_{10}$-$SM_{12}$ at the first to the third positions of the second row of the "sensing array mapping table".

In summary, the exemplary embodiments of the disclosure provide a detachable control system including the control platform 110 and a plurality of the target modules $SM_1$-$SM_n$. The control platform 110 has a sensing array mapping table. Each of the target modules $SM_1$-$SM_n$ has at least a sensing unit, where the sensing unit can detect to obtain a sensing result. The sensing results can be transmitted to the control platform 110, and the sensing results transmitted by the target modules $SM_1$-$SM_n$ can be compared and analysed according to the sensing array mapping table of the control platform 110. Therefore, the target modules can be flexibly assembled as sensing areas of different sizes according to application and environment requirements, which can be used to sense mattresses or floor of different sizes.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A control system, comprising:
n target modules $SM_1$-$SM_n$, respectively having at least a data transmission end, at least a power input end and at least a power output end, the data transmission ends of the target modules $SM_1$-$SM_n$ being electrically connected to a control platform, wherein the power input end of the target module $SM_1$ receives an operation electrical energy, the target module $SM_1$ delays the operation electrical energy by a first period, and outputs the operation electrical energy via the power output end of the target module $SM_1$, the power input end of the target module $SM_i$ receives the operation electrical energy from the power output end of the target module $SM_{(i-1)}$, the target module $SM_i$ delays the operation electrical energy by an $i^{th}$ period, and outputs the operation electrical energy via the power output end of the target module $SM_i$, wherein, the target module $SM_i$ is powered by the operation electrical energy of the power input end of the target module $SM_i$, n, i are integers, and $1 \leq i \leq n$,
wherein during an initial stage of a powered period that the power input end of the target module $SM_i$ receives the operation electrical energy, the target module $SM_i$ transmits an initialization packet to the control platform through the data transmission end of the target module $SM_i$, and the control platform obtains a layout position of the target modules $SM_i$-$SM_n$ according to a time sequence that the target modules $SM_i$-$SM_n$ output the initialization packets, and
wherein the $i^{th}$ period comprises a time required for preparing the initialization packet by the target module $SM_i$.

2. The control system as claimed in claim 1, wherein the operation electrical energy supplies electrical energy required by the target module $SM_i$ for executing a sensing operation.

3. The control system as claimed in claim 1, wherein a time period from when the target module $SM_{(i-1)}$ outputs the initialization packet to the control platform to a time when the target module $SM_i$ outputs the initialization packet to the control platform is defined as a message waiting time; when the message waiting time is smaller than a first threshold, the control platform sets the target module $SM_{(i-1)}$ and the target module $SM_i$ to be in a same row in a layout of the target modules $SM_1$-$SM_n$; when the message waiting time is greater than the first threshold and smaller than a second threshold, the control platform sets the target module $SM_{(i-1)}$ and the target module $SM_i$ to be in different rows in the layout of the target modules $SM_1$-$SM_n$.

4. The control system as claimed in claim 3, wherein when a time that the control platform waits for an initialization packet of a next target module after receiving the initialization packet of the target module $SM_i$ is greater than the second threshold, the control platform sets the target module $SM_i$ to be a last target module in the layout of the target modules $SM_1$-$SM_n$.

5. The control system as claimed in claim 1, wherein the target module $SM_i$ comprises:
a sensing unit, connected to the data transmission end of the target module $SM_i$; and a power delay circuit, having an input end connected to the power input end of the target module $SM_i$ for receiving the operation electrical energy, and after delaying by the $i^{th}$ period, an output end of the power delay circuit supplying the operation electrical energy to the sensing unit and the power output end of the target module $SM_i$.

6. The control system as claimed in claim 5, wherein the power delay circuit is a delay-on relay.

7. The control system as claimed in claim 5, wherein the power delay circuit is a controlled switch, and the controlled switch of the target module $SM_i$ is controlled by the control unit of the target module $SM_{(i-1)}$.

8. The control system as claimed in claim 5, wherein the sensing unit comprises:
   a driving unit, for driving at least one sensor to obtain a sensing result;
   a control unit, connected to the driving unit and receiving the sensing result provided by the driving unit; and
   a network unit, connected to the control unit and the data transmission end of the target module $SM_i$, for transmitting the sensing result provided by the control unit to the control platform.

9. The control system as claimed in claim 1, wherein the target module $SM_i$ comprises:
   a sensing unit, connected to the data transmission end of the target module $SM_i$; and
   a power delay circuit, wherein the power input end of the target module $SM_i$ supplies the operation electrical energy to the sensing unit and an input end of the power delay circuit, and after delaying by the $i^{th}$ period, an output end of the power delay circuit supplies the operation electrical energy to the power output end of the target module $SM_i$.

10. The control system as claimed in claim 9, wherein the power delay circuit is a delay-on relay.

11. The control system as claimed in claim 9, wherein the power delay circuit is a controlled switch, and the controlled switch is controlled by the control unit.

12. The control system as claimed in claim 9, wherein the sensing unit comprises:
   a driving unit, for driving at least one sensor to obtain a sensing result;
   a control unit, connected to the driving unit and receiving the sensing result provided by the driving unit; and
   a network unit, connected to the control unit and the data transmission end of the target module $SM_i$, for transmitting the sensing result provided by the control unit to the control platform.

13. A method for initializing a control system, wherein the control system comprises n target modules $SM_1$-$SM_n$ respectively having at least a data transmission end, at least a power input end and at least a power output end, and the method for initializing the control system comprising:
   supplying an operation electrical energy to the power input end of the target module $SM_1$;
   delaying the operation electrical energy by a first period by the target module $SM_1$, and outputting the operation electrical energy through the power output end of the target module $SM_1$;
   receiving the operation electrical energy output from the power output end of the target module $SM_{(i-1)}$ by the power input end of the target module $SM_i$; and
   delaying the operation electrical energy by an $i^{th}$ period by the target module $SM_i$, and outputting the operation electrical energy through the power output end of the target module $SM_i$, wherein, the target module $SM_i$ is powered by the operation electrical energy of the power input end of the target module $SM_i$, n and i are integers, and $1 \leq i \leq n$, wherein during an initial stage of a powered period that the power input end of the target module $SM_i$ receives the operation electrical energy, the target module $SM_i$ transmits an initialization packet to the control platform through the data transmission end of the target module $SM_i$, and the control platform obtains a layout position of the target modules $SM_1$-$SM_n$ according to a time sequence that the target modules $SM_1$-$SM_n$ output the initialization packets, and wherein the $i^{th}$ period comprises a time required for preparing the initialization packet by the target module $SM_i$.

14. The method for initializing the control system as claimed in claim 13, further comprising:
   defining a time period from when the target module $SM_{(i-1)}$ outputs the initialization packet to a time when the target module $SM_i$ outputs the initialization packet as a message waiting time;
   setting the target module $SM_{(i-1)}$ and the target module $SM_i$ to be in a same row in a layout of the target modules $SM_1$-$SM_n$ when the message waiting time is smaller than a first threshold; and
   setting the target module $SM_{(i-1)}$ and the target module $SM_i$ to be in different rows in the layout of the target modules $SM_1$-$SM_n$ when the message waiting time is greater than the first threshold and smaller than a second threshold.

15. The method for initializing the control system as claimed in claim 14, further comprising:
   setting the target module $SM_i$ to be a last target module in the layout of the target modules $SM_1$-$SM_n$ when none target module outputs an initialization packet during a time of the second threshold after the initialization packet of the target module $SM_i$ is received.

16. A control system comprising:
   n target modules $SM_1$-$SM_n$, respectively having at least a data transmission end, at least a power input end, at least a power output end, at least a power enable end and at least a power control end, wherein the data transmission ends of the target modules $SM_1$-$SM_n$ are electrically connected to a control platform, the power input end of the target module $SM_1$ receives an operation electrical energy, the power output end of the target module $SM_1$ outputs the operation electrical energy, and the power enable end of the target module $SM_1$ is electrically connected to the control platform; the power input end of the target module $SM_i$ receives the operation electrical energy from the power output end of a target module $SM_{(i-1)}$, the power output end of the target module $SM_i$ outputs the operation electrical energy, and the power enable end of the target module $SM_i$ is electrically connected to the power control end of the target module $SM_{(i-1)}$, wherein the target module $SM_i$ is powered by the operation electrical energy of the power input end of the target module $SM_i$, n and i are integers, and $1 \leq i \leq n$; and it is determined whether or not to activate the target module $SM_i$ according to control of the power enable end of the target module $SM_i$, and the power control end of the target module $SM_i$ outputs a power enable signal after the target module $SM_i$ is activated for an $i^{th}$ period, wherein during an initial stage that the target module $SM_i$ is activated, the target module $SM_i$ transmits an initialization packet to the control platform through the data transmission end of the target module $SM_i$, and the control platform obtains a layout position of the target modules $SM_i$-$SM_n$ according to a time sequence that the target modules $SM_i$-$SM_n$ output the initialization packets, and wherein the $i^{th}$ period comprises a time required for preparing the initialization packet by the target module $SM_i$.

17. The control system as claimed in claim 16, wherein the operation electrical energy supplies electrical energy required by the target module $SM_i$ for executing a sensing operation.

18. The control system as claimed in claim 16, wherein a time period from when the target module $SM_{(i-1)}$ outputs the initialization packet to the control platform to a time when the target module $SM_i$ outputs the initialization packet to the control platform is defined as a message waiting time; when the message waiting time is smaller than a first threshold, the control platform sets the target module $SM_{(i-1)}$ and the target module $SM_i$ to be in a same row in a layout of the target modules $SM_1$-$SM_n$; when the message waiting time is greater than the first threshold and smaller than a second threshold, the control platform sets the target module $SM_{(i-1)}$ and the target module $SM_i$ to be in different rows in the layout of the target modules $SM_1$-$SM_n$.

19. The control system as claimed in claim 18, wherein when a time that the control platform waits for an initialization packet of a next target module after receiving the initialization packet of the target module $SM_i$ is greater than the second threshold, the control platform sets the target module $SM_i$ to be a last target module in the layout of the target modules $SM_1$-$SM_n$.

20. The control system as claimed in claim 16, wherein the target module $SM_i$ comprises:

a sensing unit, connected to the data transmission end of the target module $SM_i$; and a power delay circuit, having an input end connected to the power input end and the power output end of the target module $SM_i$ for receiving the operation electrical energy, and determining whether or not to supply the operation electrical energy to the sensing unit through an output end according to control of a control end of the power delay circuit, wherein after delaying by the $i^{th}$ period, the sensing unit outputs the power enable signal to the power control end of the target module $SM_i$.

21. The control system as claimed in claim 20, wherein the power delay circuit is a switch and/or a voltage regulator.

22. The control system as claimed in claim 20, wherein the sensing unit comprises:

a driving unit, for driving at least one sensor to obtain a sensing result;

a control unit, connected to the driving unit and receiving the sensing result provided by the driving unit, and outputting the power enable signal after being activated for an $i^{th}$ period; and a network unit, connected to the control unit and the data transmission end of the target module $SM_i$, for transmitting the sensing result provided by the control unit to the control platform.

23. A control system, comprising:

n target modules $SM_1$-$SM_n$, respectively having at least a data transmission end, at least a power input end and at least a power out end, the data transmission ends of the target modules $SM_1$-$SM_n$ being electrically connected to a control platform, wherein the power input end of the target module $SM_1$ receives an operation electrical energy, the target module $SM_1$ delays the operation electrical energy by a first period, and outputs the operation electrical energy via the power output end of the target module $SM_1$, the power input end of the target module $SM_i$ receives the operation electrical energy from the power output end of the target module $SM_{(i-1)}$, the target module $SM_i$ delays the operation electrical energy by an $i^{th}$ period, and outputs the operation electrical energy via the power output end of the target module $SM_i$, wherein the target module $SM_i$ is powered by the operation electrical energy of the power input end of the target module $SM_i$, n, i are intergers, and $1 \leq i \leq n$, wherein during an initial stage of a powering period that the power output end of the target module $SM_i$ outputs the operation electrical energy, the target module $SM_i$ transmits an initialization packet to the control platform through the data transmission end of the target module $SM_i$, and the control platform obtains a layout position of the target modules $SM_i$-$SM_n$, according to a time sequence that the target modules $SM_1$-$SM_n$ output the initialization packets; and wherein the $i^{th}$ period comprises a time required for preparing the initialization packet by the target module $SM_{(i-1)}$.

24. A control system, comprising:

n target modules $SM_1$-$SM_n$, respectively having at least a data transmission end, at least a power input end and at least a power output end, the data transmission ends of the target modules $SM_1$-$SM_n$ being electrically connected to a control platform, wherein the power input end of the target module $SM_1$ receives an operation electrical energy, the target module $SM_1$ delays the operation electrical energy by a first period, and outputs the operation electrical energy via the power output end of the target module $SM_1$, the power input end of the target module $SM_i$, receives the operation electrical energy from the power output end of the target module $SM_{(i-1)}$, the target module $SM_i$ delays the operation electrical energy by an $i^{th}$ period, and outputs the operation electrical energy via the power output end of the target module $SM_i$, wherein the target module $SM_i$ is powered by the operation electrical energy of the power input end of the target module $SM_i$, n, i are integers, and $1 \leq i \leq n$, wherein a time period from when the target module $SM_{(i-1)}$ outputs the initialization packet to the control platform to a time when the target module $SM_i$ outputs the initialization packet to the control platform is defined as a message waiting time; when the message waiting time is smaller than a first threshold, the control platform sets the target module $SM_{(i-1)}$ and the target module $SM_i$ to be in a same row in a layout of the target modules $SM_i$-$SM_n$; when the message waiting time is greater than the first threshold and smaller than a second threshold, the control platform sets the target module $SM_{(i-1)}$ and the target module $SM_i$ to be in different rows in the layout of the target modules $SM_1$-$SM_n$.

25. A method for initializing a control system, wherein the control system comprises n target modules $SM_1$-$SM_n$ respectively having at least a data transmission end, at least a power input end and at least a power output end, and the method for initializing the control system comprising:

supplying an operation electrical energy to the power input end of the target module $SM_1$;

delaying the operation electrical energy by a first period by the target module $SM_1$, and outputting the operation electrical energy through the power output end of the target module $SM_1$;

receiving the operation electrical energy output from the power output end of the target module $SM_{(i-1)}$ by the power input end of the target module $SM_i$; and delaying the operation electrical energy by an ith period by the target module $SM_i$, and outputting the operation electrical energy through the power output end of the target module $SM_i$, wherein the target module $SM_i$ is powered by the operation electrical energy of the power input end of the target module $SM_i$, n and i are integers, and $1 \leq i \leq n$, wherein during an initial stage of a powering period that the power output end of the target module $SM_i$ outputs the operation electrical energy, the target module $SM_i$ transmits an initialization packet to the control platform through the data transmission end of the target module $SM_i$, and the control platform obtains a layout position of the target modules $SM_1$-$SM_n$, according to a time sequence that the target modules $SM_1$-$SM_n$ output the initialization packets; and wherein the $i^{th}$ period comprises a time required for preparing the initialization packet by the target module $SM_{(i-1)}$.

26. A method for initializing a control system, wherein the control system comprises n target modules $SM_1$-$SM_n$ respectively having at least a data transmission end, at least a power input end and at least a power output end, and the method for initializing the control system comprising:

supplying an operation electrical energy to the power input end of the target module $SM_1$;

delaying the operation electrical energy by a first period by the target module $SM_1$, and outputting the operation electrical energy through the power output end of the target module $SM_1$;

receiving the operation electrical energy output from the power output end of the target module $SM_{(i-1)}$ by the power input end of the target module $SM_i$;

delaying the operation electrical energy by an ith period by the target module $SM_i$, and outputting the operation electrical energy through the power output end of the target module $SM_i$ wherein the target module $SM_i$ is powered by the operation electrical energy of the power input end of the target module $SM_i$, n and i are integers, and $1 \leq i \leq n$;

defining a time period from when the target module $SM_{(i-1)}$ outputs the initialization packet to a time when the target module $SM_i$ outputs the initialization packet as a message waiting time;

setting the target module $SM_{(i-1)}$ and the target module $SM_i$ to be in a same row in a layout of the target modules $SM_1$-$SM_n$ when the message waiting time is smaller than a first threshold; and setting the target module $SM_{(i-1)}$ and the target module $SM_i$ to be in different rows in the layout of the target modules $SM_1$-$SM_n$ when the message waiting time is greater than the first threshold and smaller than a second threshold.

27. A control system comprising:

n target modules $SM_1$-$SM_n$, respectively having at least a data transmission end, at least a power input end, at least a power output end, at least a power enable end and at least a power control end, wherein the data transmission ends of the target modules $SM_1$-$SM_n$ are electrically connected to a control platform, the power input end of the target module $SM_1$ receives an operation electrical energy, the power output end of the target module $SM_1$ outputs the operation electrical energy, and the power enable end of the target module $SM_1$ is electrically connected to the control platform; the power input end of the target module $SM_i$ receives the operation electrical energy from the power output end of a target module $SM_{(i-1)}$, the power output end of the target module $SM_i$ outputs the operation electrical energy, and the power enable end of the target module $SM_i$ is electrically connected to the power control end of the target module $SM_{(i-1)}$, wherein the target module $SM_i$ is powered by the operation electrical energy of the power input end of the target module $SM_i$, n and i are integers, and $1 \leq i \leq n$; and it is determined whether or not to activate the target module $SM_i$ according to control of the power enable end of the target module $SM_i$, and the power control end of the target module $SM_i$ outputs a power enable signal after the target module $SM_i$ is activated for an $i^{th}$ period, wherein a time period from when the target module $SM_{(i-1)}$ outputs the initialization packet to the control platform to a time when the target module $SM_i$ outputs the initialization packet to the control platform is defined as a message waiting time; when the message waiting time is smaller than a first threshold, the control platform sets the target module $SM_{(i-1)}$ and the target module $SM_i$ to be in a same row in a layout of the target modules $SM_1$-$SM_n$; when the message waiting time is greater than the first threshold and smaller than a second threshold, the control platform sets the target module $SM_{(i-1)}$ and the target module $SM_i$ to be in different rows in the layout of the target modules $SM_1$-$SM_n$.

* * * * *